United States Patent
Yoshida et al.

(10) Patent No.: US 12,150,711 B2
(45) Date of Patent: Nov. 26, 2024

(54) BLOOD FLOW ANALYSIS APPARATUS, BLOOD FLOW ANALYSIS METHOD, AND RECORDING MEDIUM

(71) Applicants: National University Corporation ASAHIKAWA MEDICAL UNIVERSITY, Asahikawa (JP); Topcon Corporation, Tokyo (JP)

(72) Inventors: Akitoshi Yoshida, Asahikawa (JP); Kana Minamide, Tokyo (JP); Masahiro Akiba, Toda (JP); Jun Sakai, Kuki (JP)

(73) Assignees: NATIONAL UNIVERSITY CORPORATION ASAHIKAWA MEDICAL UNIVERSITY, Asahikawa (JP); TOPCON CORPORATION, Tokyo (JP)

( * ) Notice: Subject to any disclaimer, the term of this patent is extended or adjusted under 35 U.S.C. 154(b) by 822 days.

(21) Appl. No.: 17/319,089

(22) Filed: May 13, 2021

(65) Prior Publication Data

US 2021/0386290 A1    Dec. 16, 2021

(30) Foreign Application Priority Data

Jun. 11, 2020    (JP) ................................. 2020-101391

(51) Int. Cl.
*A61B 3/12* (2006.01)
*A61B 3/10* (2006.01)

(52) U.S. Cl.
CPC ............ *A61B 3/1241* (2013.01); *A61B 3/102* (2013.01)

(58) Field of Classification Search
CPC ..... A61B 3/1241; A61B 3/102; A61B 3/0025; A61B 5/0261; A61B 5/0285
USPC ........................................................ 351/206
See application file for complete search history.

(56) References Cited

U.S. PATENT DOCUMENTS

2015/0313466 A1* 11/2015 Yoshida ................. G06T 11/60
600/425

FOREIGN PATENT DOCUMENTS

| JP | 8-215150 A | 8/1996 |
|---|---|---|
| JP | 2017-79886 A | 5/2017 |
| JP | 2019-42264 A | 3/2019 |
| WO | 2007/132865 A1 | 11/2007 |
| WO | 2008/069062 A1 | 6/2008 |
| WO | 2010/131550 A1 | 11/2010 |

OTHER PUBLICATIONS

JP 2019042264; Kota et al. Ophthalmologic imaging apparatus and ophthalmologic information processing apparatus (Examiner provided machine translation of JP 2019042264) (Year: 2019).*

(Continued)

*Primary Examiner* — Tuyen Tra
*Assistant Examiner* — Rahman Abdur
(74) *Attorney, Agent, or Firm* — XSENSUS LLP

(57) ABSTRACT

The blood flow analysis apparatus includes an acquisition unit and an extractor. The acquisition unit is configured to acquire blood flow information representing time-course changes in a blood flow velocity of a single retinal artery or retinal vein. The extractor is configured to extract one or more parameters corresponding to change in the blood flow velocity from the blood flow information.

15 Claims, 16 Drawing Sheets

(56) References Cited

OTHER PUBLICATIONS

BR PI0513843; Muller et al. Compound Or A Pharmaceutically Acceptable Salt Or Solvate Or Prodrug Thereof, Pharmaceutical Composition, Dosage Form, Use Of A Compound; (Examiner provided machine translation of BR PI0513843) (Year: 2008).*
Luft et al., Ocular Blood Flow Measurements in Healthy White Subjects Using Laser Speckle Flowgraphy, PLoS One, vol. 11, Issue 12, Dec. 13, 2016, pp. 1-17.
Japanese Office Action issued Dec. 12, 2023, in corresponding Japanese Patent Application No. 2020-101391, 6 pages.

* cited by examiner (a) Area total (b) Area Elevation (c) Area Declination (a) Area Systolic (b) S1

(c) S2

(a) Area Diastolic (b) D1

(c) D2

BLOOD FLOW ANALYSIS APPARATUS, BLOOD FLOW ANALYSIS METHOD, AND RECORDING MEDIUM

CROSS-REFERENCE TO RELATED APPLICATION

This application is based upon and claims the benefit of priority from Japanese Patent Application No. 2020-101391, filed Jun. 11, 2020, the entire contents of which are incorporated herein by reference.

FIELD

The disclosure relates to a blood flow analysis apparatus, a blood flow analysis method, and a recording medium.

BACKGROUND

Evaluation of the dynamics of the general circulation is useful for the diagnosis and prophylaxis of circulatory condition such as arteriosclerosis. The dynamics of the general circulation is evaluated using waveform of the blood pressure, for example. On the other hand, in recent years, attention has been focused on methods for evaluating the relationship between retinal blood flow amount and the dynamics of the general circulation.

For example, "Ocular Blood Flow Measurements in Healthy White Subjects Using Laser Speckle Flowgraphy" (Nikolaus Luft et al., PLOS ONE, Dec. 13, 2016, DOI: 10.1371/journal.pone.0168190) discloses a method of measuring the blood flow amount based on the change in speckle pattern caused by red blood cells flowing in blood vessels exiting from the optic disc using the laser speckle flowgraphy, and of evaluation the age dependence from the measured blood flow amount.

SUMMARY

One aspect of some embodiments is a blood flow analysis apparatus, including: an acquisition unit configured to acquire blood flow information representing time-course changes in a blood flow velocity of a single retinal artery or a single retinal vein; and an extractor configured to extract one or more parameters corresponding to change in the blood flow velocity from the blood flow information.

Another aspect of some embodiments is a blood flow analysis method, including: an acquisition step of acquiring blood flow information representing time-course changes in a blood flow velocity of a single retinal artery or a single retinal vein; and an extraction step of extracting one or more parameters corresponding to change in the blood flow velocity from the blood flow information.

Still another aspect of some embodiments is a computer readable non-transitory recording medium in which a program for causing a computer to execute each step of the blood flow analysis method described above is recorded.

DETAILED DESCRIPTION

Figure 1:
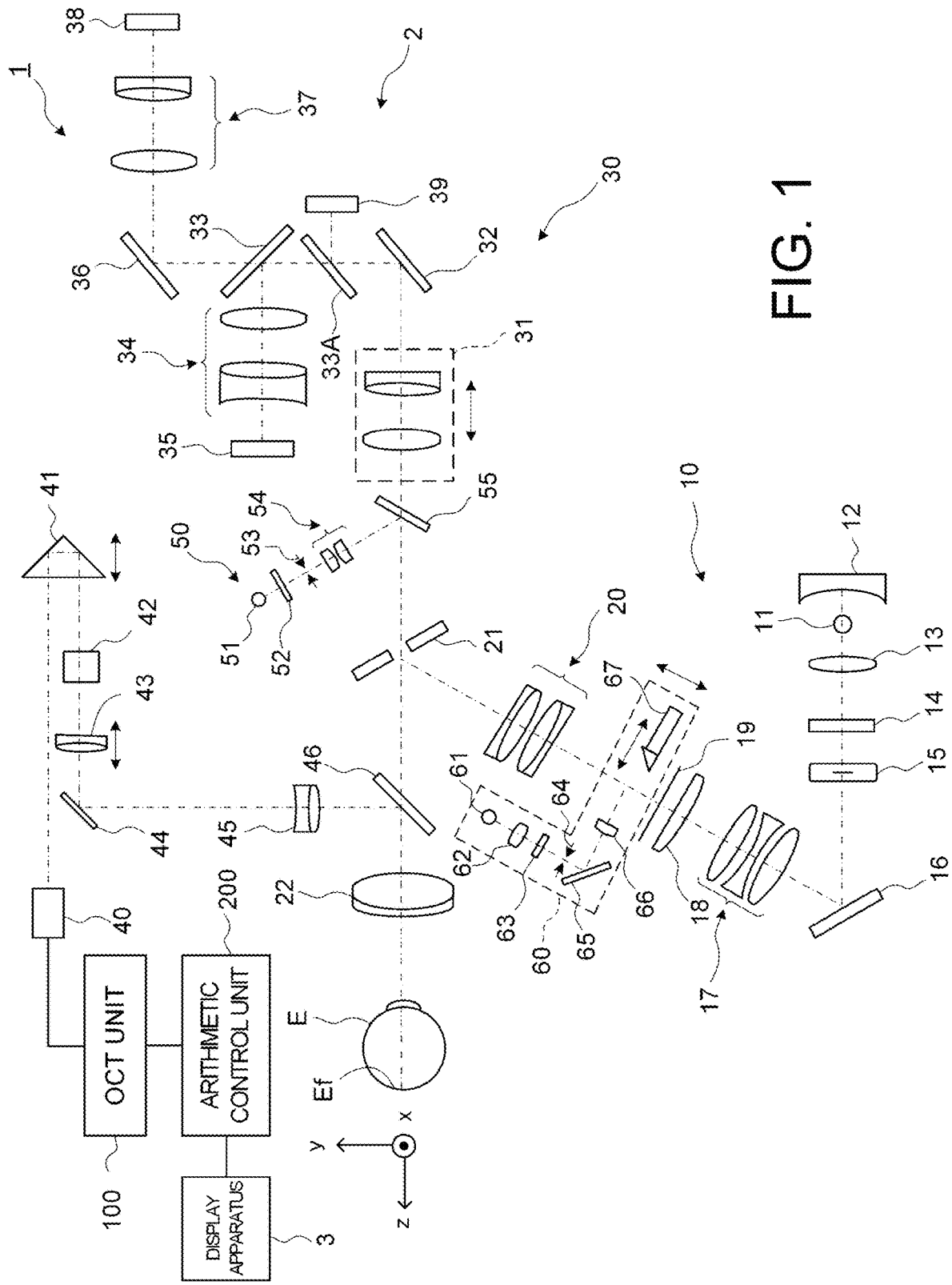
FIG. 1 is a schematic diagram illustrating an example of a configuration of a blood flow analysis apparatus according to embodiments.

The blood flow measured using the laser speckle flowgraphy includes a choroidal blood flow and a retinal blood flow. Thereby, the dynamics of the general circulation caused by the blood flow in a predetermined layer region in a fundus such as a choroidal blood flow or a retinal blood flow can not be evaluated with high accuracy.

According to some embodiments of the present invention, a new technique for evaluating the dynamics of the general circulation caused by a blood flow in a predetermined layer region in a fundus with high accuracy can be provided.

Referring now to the drawings, exemplary embodiments of a blood flow analysis apparatus, a blood flow analysis method, a program, and a recording medium are described below. Any of the contents of the documents cited in the present specification and arbitrary known techniques may be applied to the embodiments below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

A blood flow analysis apparatus according to embodiments is configured to acquire blood flow information representing time-course changes in blood flow velocity of a single artery or a single vein in a predetermined layer region in a fundus of a subject's eye, and is configured to extract one or more parameters corresponding to the change in the blood flow velocity from the acquired blood flow information. For example, the dynamics of the general circulation is evaluated based on the extracted one or more parameters. In some embodiments, the artery is a retinal artery, or the vein is a retinal vein. The retinal artery or the retinal vein is an artery or a vein in a layer region between inner limiting membrane and Bruch membrane. In some embodiments, the artery is a choroidal artery, or the vein is a choroidal vein. In some embodiments, the blood flow information is obtained using optical coherence tomography (OCT). In some embodiments, the blood flow analysis apparatus has a function of performing OCT for acquiring the blood flow information. In some embodiments, the blood flow analysis apparatus acquires the blood flow information by receiving the blood flow information acquired by performing OCT from outside the apparatus.

The blood flow analysis method according to the embodiments is performed by the blood flow analysis apparatus according to the embodiments. A program according to the embodiments causes a computer to execute each step of the blood flow analysis method.

In the following embodiments, a case where an ophthalmologic apparatus for performing Fourier-domain-type OCT realizes a function of the blood flow analysis apparatus according to the embodiments will be described.

In the following, the ophthalmologic apparatus that combines swept source OCT and a fundus camera will be described. However, the configuration according to the embodiments is not limited thereto. For example, the type of OCT is not limited to swept source OCT, and it may be the spectral domain OCT or the like. The swept source OCT is a technique that splits light from a wavelength tunable type (i.e., a wavelength sweep type) light source into measurement light and reference light; superposes the measurement light returning from the object to be measured with the reference light to generate interference light; detects the interference light with a balanced photodiode or the like; and applies the Fourier transform etc. to the detection data acquired through the sweeping of wavelength and the scanning of the measurement light to form an image. On the other hand, the spectral domain OCT is a technique that splits light from a low coherence light source into measurement light and reference light; superposes the measurement light returning from the object to be measured with the reference light to generate interference light; detects the spectral distribution of the interference light with a spectrometer; and applies the Fourier transform etc. to the detected spectral distribution to form an image. In other words, the swept source OCT is an method for acquiring the spectral distribution by time division, and the spectral domain OCT is an method for acquiring the spectral distribution by space division. It should be noted that the method of OCT that can be applied to the embodiments is not limited to this, and any other method (e.g., time domain OCT) can be applied.

The ophthalmologic apparatus according to the embodiments may or may not have the function to acquire photographs (digital photographs) of the subject's eye, such as a fundus camera. Further, the ophthalmologic apparatus may include an arbitrary modality such as a scanning laser ophthalmoscope (SLO), a slit lamp microscope, an anterior segment photographing camera, a surgical microscope, a photocoagulator, in place of or in addition to the fundus camera. It should be noted that a front image such as fundus photograph can be used for the observing the fundus, setting the scan area, tracking, or the like.

<Configuration>

As shown in FIG. 1, the ophthalmologic apparatus 1 includes a fundus camera unit 2, an OCT unit 100, and an arithmetic control unit 200. The fundus camera unit 2 has substantially the same optical system as the conventional fundus camera. The OCT unit 100 is provided with an optical system and a mechanism for performing OCT. The arithmetic control unit 200 includes a processor. A chin rest and a forehead pad for supporting the subject's face are provided at positions facing the fundus camera unit 2.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

<Optical System>

[Fundus Camera Unit 2]

The fundus camera unit 2 is provided with an optical system for imaging (photographing) a fundus Ef of the subject's eye E. Examples of an image (called fundus image, fundus photograph, etc.) of the fundus Ef obtained by photographing the fundus Ef include an observation image and a captured image (photographed image). The observation image is, for example, obtained by moving image shooting using near infrared light. The captured image is, for example, a color image or monochrome image captured by visible flash light, or a monochrome image captured using near-infrared flash light. The fundus camera unit 2 may be configured to be capable of acquiring fluorescein fluorescence images, indocyanine green images, or autofluorescent images.

The fundus camera unit 2 includes an illumination optical system 10 and an imaging (photographing) optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

An observation light source 11 in the illumination optical system 10 includes, for example, a halogen lamp or a light-emitting diode (LED). Light (observation illumination light) emitted from the observation light source 11 is reflected by a reflective mirror 12 having a curved reflective surface, and becomes near-infrared light after passing through a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of the aperture part) of the perforated mirror 21, is transmitted through the dichroic mirror 46, and refracted by the objective lens 22, thereby illuminating the fundus Ef.

Returning light of the observation illumination light reflected from the subject's eye E is refracted by the objective lens 22, is transmitted through the dichroic mirror 46, passes through the hole part formed in the center region of the perforated mirror 21. The returning light passing through the dichroic mirror 55 travels through a imaging focusing lens 31 and is reflected by a mirror 32. Further, this returning light is transmitted through a half mirror 33A, is reflected by a dichroic mirror 33, and forms an image on the light receiving surface of an image sensor 35 by a condenser lens 34. The image sensor 35 detects the returning light at a predetermined frame rate, for example. It should be noted that when the imaging optical system 30 is in focus on the fundus Ef, the observation image of the fundus Ef is obtained, and when the imaging optical system 30 is in focus on the anterior segment, the observation image of the anterior segment is obtained.

The imaging light source 15 is a visible light source including a xenon lamp or an LED, for example. Light (imaging illumination light) emitted from the imaging light source 15 is projected onto the fundus Ef via the same route as that of the observation illumination light. Returning light of the imaging illumination light from the subject's eye E is guided to the dichroic mirror 33 via the same route as that of the observation illumination light, is transmitted through the dichroic mirror 33, is reflected by a mirror 36, and forms an image on the light receiving surface of the image sensor 38 by a condenser lens 37.

A liquid crystal display (LCD) 39 displays a fixation target for fixating the subject's eye E. Part of light flux (fixation light flux) output from the LCD 39 is reflected by the half mirror 33A, is reflected by the mirror 32, travels through the imaging focusing lens 31 and the dichroic mirror 55, and passes through the hole part of the perforated mirror 21. The fixation light flux having passed through the hole part of the perforated mirror 21 is transmitted through the dichroic mirror 46, and is refracted by the objective lens 22, thereby being projected onto the fundus Ef. By changing the display position of the fixation target on the screen of the LCD 39, the fixation position of the subject's eye E can be changed. It should be noted that instead of the LCD 39, a matrix LED with a two-dimensional array of a plurality of LEDs or a combination of a light source and a variable aperture (such as a liquid crystal aperture) can be used as a means of generating a fixation light flux.

The fundus camera unit 2 is provided with an alignment optical system 50 and a focus optical system 60. The alignment optical system 50 generates an alignment indicator for alignment of the optical system with respect to the subject's eye E. The focus optical system 60 generates a split indicator for adjusting the focus with respect to the subject's eye E.

Alignment light output from an LED 51 of the alignment optical system 50 travels through the diaphragms 52 and 53 and the relay lens 54, is reflected by the dichroic mirror 55, and passes through the hole part of the perforated mirror 21. The light having passed through the hole part of the perforated mirror 21 is transmitted through the dichroic mirror 46, and is projected onto the subject's eye E by the objective lens 22.

Cornea reflection light of the alignment light travels through the objective lens 22, the dichroic mirror 46 and the hole part described above. Part of the cornea reflection light is transmitted through the dichroic mirror 55, and passes through the imaging focusing lens 31. The cornea reflection light having passed through the imaging focusing lens 31 is reflected by the mirror 32, is transmitted through the half mirror 33A, is reflected by the dichroic mirror 33, and is projected onto the light receiving surface of the CCD image sensor 35 by the condenser lens 34. Based on the received light image (alignment indicator image consisting of two bright spots) obtained by the CCD image sensor 35, manual alignment as before or automatic alignment as before can be performed.

The focus optical system 60 is movable along an optical path (illumination optical path) of the illumination optical system 10 in conjunction with the movement of the imaging focusing lens 31 along an optical path (imaging optical path) of the imaging optical system 30. The reflection rod 67 can be inserted and removed into and from the illumination optical path.

To perform focus adjustment, the reflective surface of the reflection rod 67 is arranged in a slanted into the illumination optical path. Focus light emitted from an LED 61 passes through a relay lens 62, is split into two light fluxes by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, is transmitted through the dichroic mirror 46, and is refracted by the objective lens 22, thereby being projected onto the fundus Ef.

Fundus reflection light of the focus light passes through the same route as the cornea reflection light and is detected by the CCD image sensor 35. Based on the received light image (alignment indicator image consisting of two image) obtained by the CCD image sensor 35, manual alignment as before or automatic alignment as before can be performed.

The dichroic mirror 46 combines an optical path for fundus imaging and an optical path for OCT. The dichroic mirror 46 reflects light of wavelength band used in OCT, and transmits light for fundus imaging. The optical path for OCT is provided with, in order from the OCT unit 100 side, the collimator lens unit 40, the optical path length (OPL) changing unit 41, the optical scanner 42, the OCT focusing lens 43, the mirror 44, and the relay lens 45.

The optical path length changing unit 41 is movable in directions indicated by the arrow in FIG. 1, thereby changing the optical length of the optical path for OCT. The change in the optical path length is used for the correction of the optical path length according to the axial length of the subject's eye E, for the adjustment of the interference state, or the like. The optical path length changing unit 41 includes a corner cube and a mechanism for moving the corner cube, for example.

The optical scanner 42 is disposed at a position optically conjugate with the pupil of the subject's eye E. The optical scanner 42 changes the traveling direction of measurement light LS traveling along the OCT optical path. With this, the subject's eye E can be scanned with the measurement light LS. The optical scanner 42 can deflect the measurement light LS in any direction of the xy-plane. The optical scanner 42 includes, for example, a galvano mirror that deflects the measurement light LS in the x direction and a galvano mirror that deflects the measurement light LS in the y direction.

[OCT Unit 100]

Figure 2:
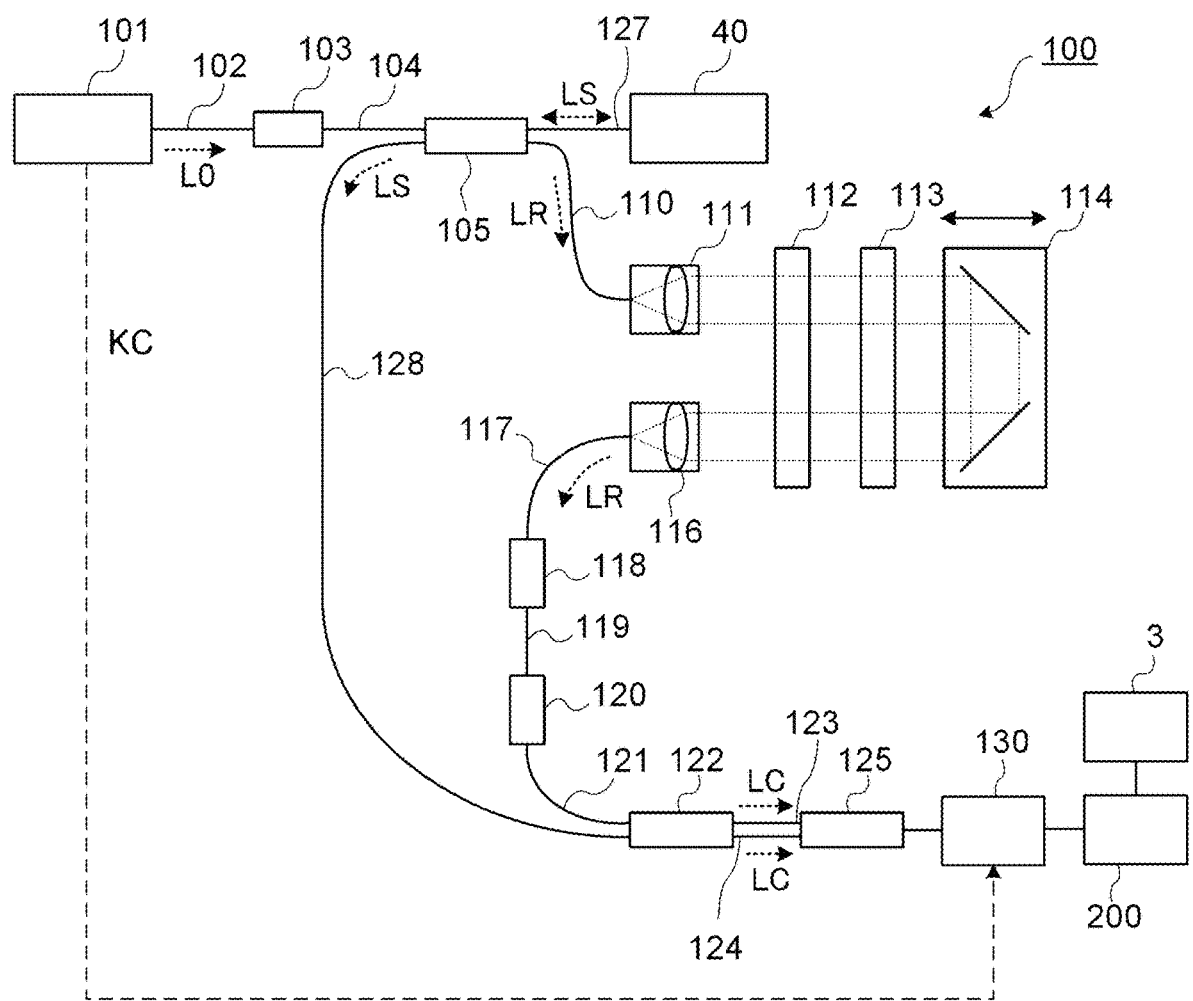
FIG. 2 is a schematic diagram illustrating an example of the configuration of the blood flow analysis apparatus according to the embodiments.

As illustrated by an example in FIG. 2, the OCT unit 100 is provided with an optical system for performing OCT on the subject's eye E. The configuration of this optical system is the same as that of conventional swept source OCT. That is, the optical system is an interference optical system that splits light from the light source into measurement light and reference light, makes returning light of the measurement light from the subject's eye E and the reference light having traveled through a reference optical path interfere with each other to generate interference light, and detects the interference light. The detection result (detection signal) of the interference light obtained by the interference optical system is a signal indicating a spectrum of the interference light, and is sent to the arithmetic control unit 200.

Like the general swept source OCT, the light source unit 101 includes a wavelength tunable light source capable of changing the wavelength of emitted light at high speed. The wavelength tunable light source is a near-infrared laser light source, for example.

The light LO emitted from the light source unit 101 is guided to the polarization controller 103 through the optical fiber 102, and the polarization state of the light LO is adjusted. Further, the light LO is guided to the fiber coupler 105 through the optical fiber 104. The fiber coupler 105 splits the light LO into the measurement light LS and the reference light LR.

The reference light LR is guided to the collimator 111 through the optical fiber 110. The reference light LR is converted into a parallel light flux by the collimator 111. Then, the reference light LR is guided to the corner cube 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS.

The corner cube 114 changes the traveling direction of the incident reference light LR in the opposite direction. The incident direction of the reference light LR to the corner cube 114 and the emitting direction of the reference light LR are parallel to each other. The corner cube 114 is movable in the incident direction of the reference light LR. With this, the optical path length of the reference light LR is changed.

The configuration shown in FIG. 1 and FIG. 2 includes both the optical path length changing unit 41 that changes the optical path length of the measurement light LS (i.e., measurement optical path or measurement arm) and the corner cube 114 that changes the optical path length of the reference light LR (i.e., reference optical path or reference arm). In some embodiments, any one of the optical path length changing unit 41 and the corner cube 114 may be provided. The difference between the measurement optical path length and the reference optical path length can be changed using other optical members.

The reference light LR that has traveled through the corner cube 114 passes through the dispersion compensation member 113 and the optical path length correction member 112, is converted from the parallel light flux to the convergent light flux by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through an optical fiber 127, and is made into the parallel light flux by the collimator lens unit 40. The measurement light LS that has made into the parallel light flux is guided to the dichroic mirror 46 via the optical path length changing unit 41, the optical scanner 42, the OCT focusing lens 43, the mirror 44, and the relay lens 45. Then, the measurement light LS is refracted by the objective lens 22, and enters the subject's eye E. The measurement light LS is scattered and reflected at various depth positions of the subject's eye E. Returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC is guided to a detector 125 through optical fibers 123 and 124, respectively.

The detector 125 is a balanced photodiode, for example. The balanced photodiode includes a pair of photodetectors in which each photodetector detects each of the pair of interference light LC. The balanced photodiode outputs the difference between a pair of detection results acquired by the pair of photodetectors. The detector 125 sends the detection result (detection signal) to a DAQ (data acquisition system) 130.

A clock KC is supplied from the light source unit 101 to the DAQ 130. The clock KC is generated in the light source unit 101 in synchronization with the output timing of each wavelength within a predetermined wavelength range performed by the wavelength tunable type light source. For example, the light source unit 101 optically delays one of the two pieces of branched light obtained by branching the light LO of each output wavelength, and then generates the clock KC based on the result of the detection of the combined light of the two pieces of branched light. The DAQ 130 performs sampling the detection signal input from the detector 125 based on the clock KC. The DAQ 130 sends the result of sampling the detection signal from the detector 125 to an arithmetic control unit 200.

[Arithmetic Control Unit 200]

The arithmetic control unit 200 controls each part of the fundus camera unit 2, the display apparatus 3, and the OCT unit 100. Further, the arithmetic control unit 200 performs various arithmetic processing. For example, for each series of wavelength scans (for each A-line), the arithmetic control unit 200 performs signal processing such as Fourier transform on the spectral distribution based on the detection results obtained by the detector 125 to form a reflection intensity profile at each A-line. In addition, the arithmetic control unit 200 forms image data by applying imaging processing to the reflection intensity profiles for the respective A-lines. The arithmetic processing therefor is performed in the same manner as in the conventional swept source OCT.

The arithmetic control unit 200 includes a processor, a random access memory (RAM), a read only memory (ROM), a hard disk drive, a communication interface, and the like, for example. A storage device such as the hard disk drive stores various computer programs. The arithmetic control unit 200 may include an operation device, an input device, a display device, or the like.

<Control System>

The control system (processing system) of the ophthalmologic apparatus 1 is configured with the arithmetic control unit 200 as a center.

Figure 3:
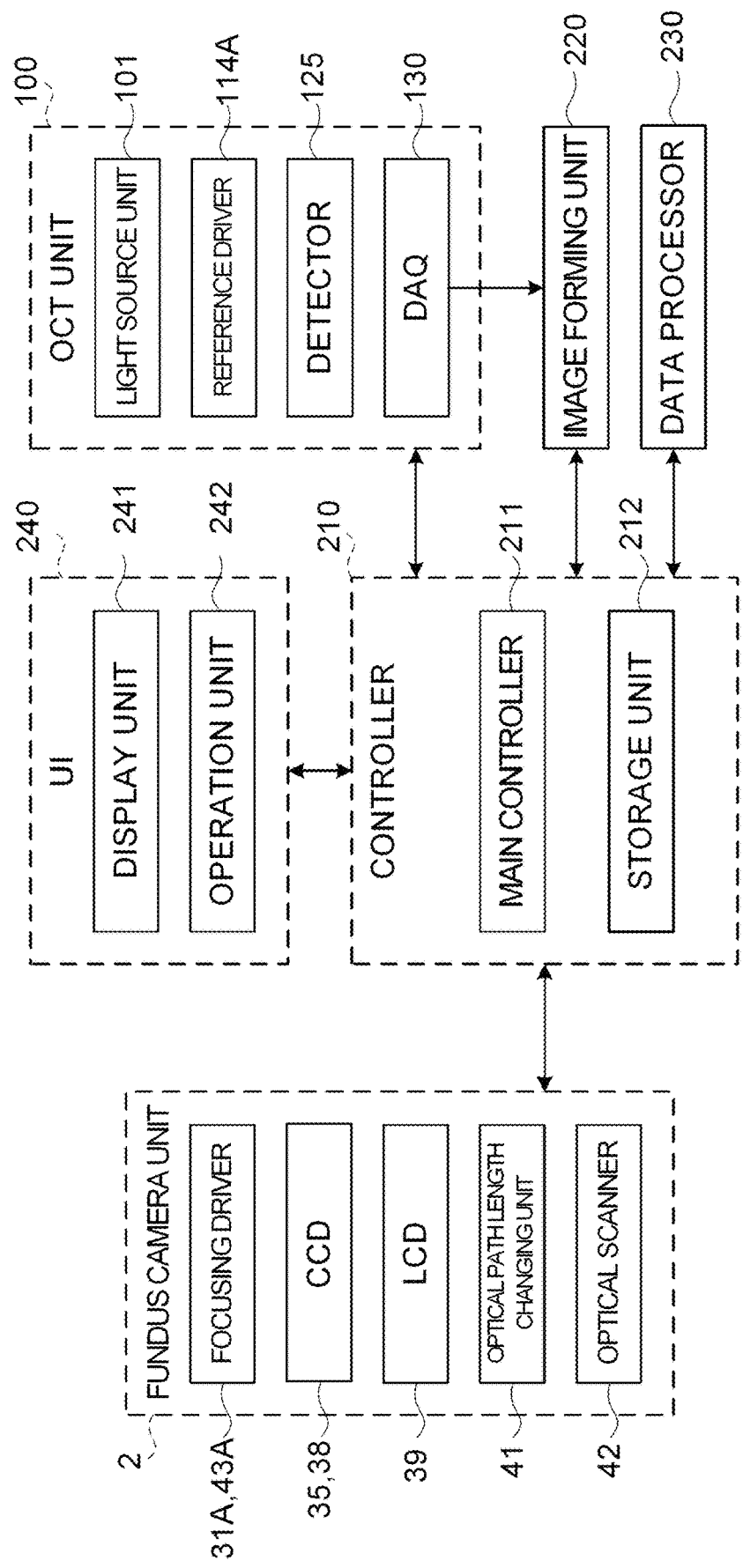
FIG. 3 is a schematic diagram illustrating an example of the configuration of the blood flow analysis apparatus according to the embodiments.
Figure 4:
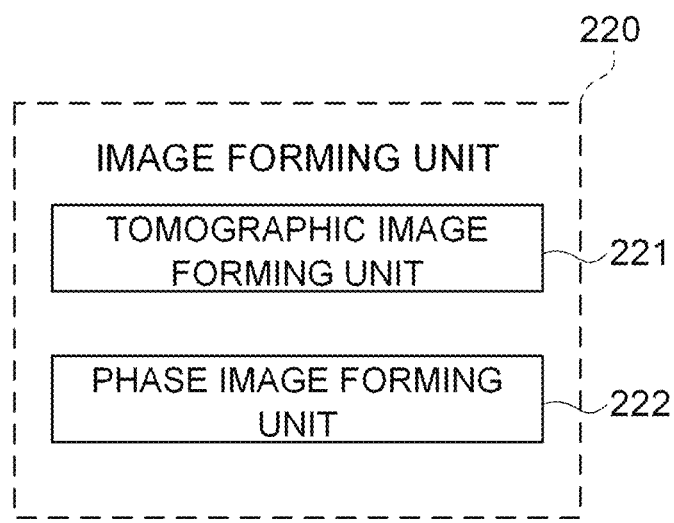
FIG. 4 is a schematic diagram illustrating an example of a configuration of a blood flow analysis apparatus according to the embodiments.
Figure 5:
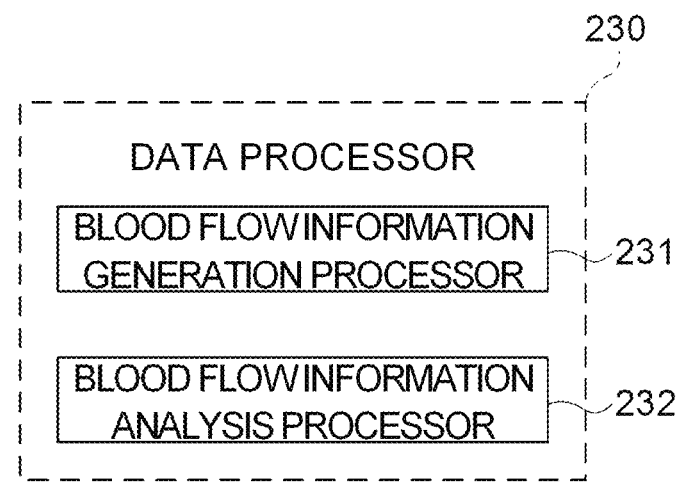
FIG. 5 is a schematic diagram illustrating an example of the configuration of the blood flow analysis apparatus according to the embodiments.
Figure 6:
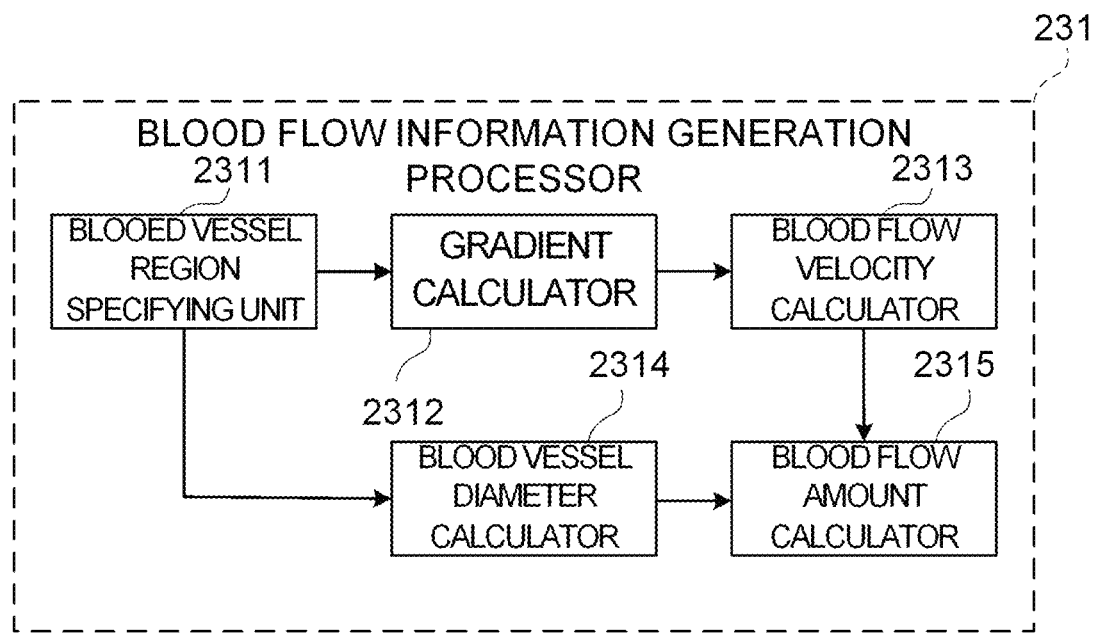
FIG. 6 is a schematic diagram illustrating an example of the configuration of the blood flow analysis apparatus according to the embodiments.
Figure 7:
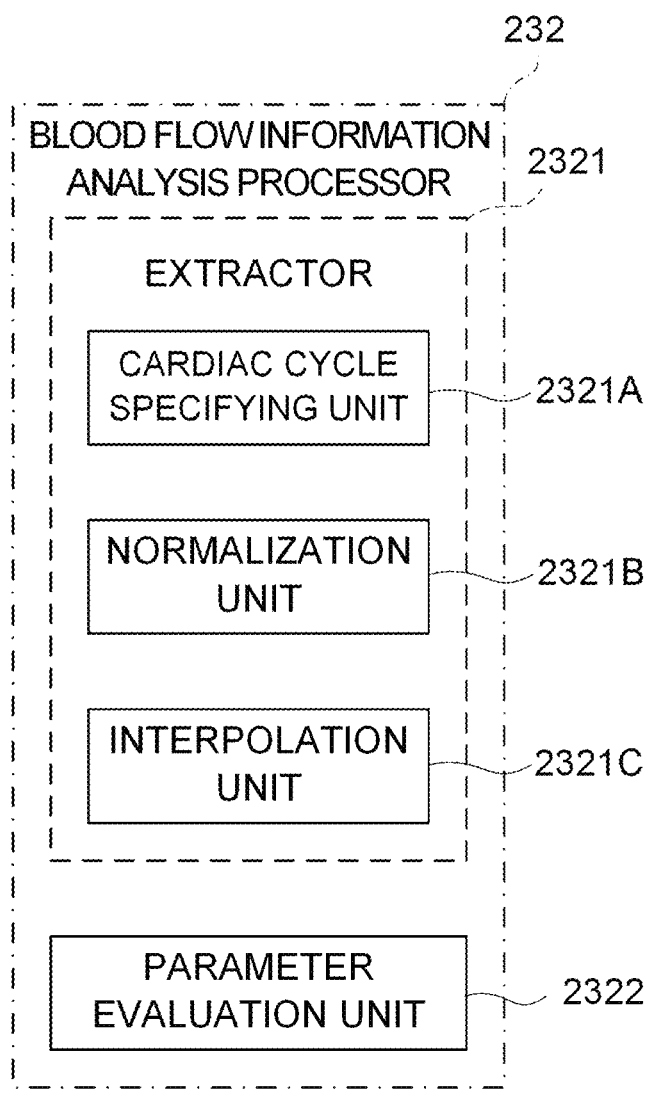
FIG. 7 is a schematic diagram illustrating an example of the configuration of the blood flow analysis apparatus according to the embodiments.

FIGS. 3 to 7 show configuration examples of the control system (processing system) of the ophthalmologic apparatus 1. FIG. 3 shows an example of a functional block diagram of the control system of the ophthalmologic apparatus 1. FIG. 4 shows an example of a functional block diagram of an image forming unit 220 in FIG. 3. FIG. 5 shows an example of a functional block diagram of a data processor 230 in FIG. 3. FIG. 6 shows an example of a functional block diagram of a blood flow information generation processor 231 in FIG. 5. FIG. 7 shows example of a functional block diagram of a blood flow information analysis processor 232 in FIG. 5.

The arithmetic control unit 200 includes a controller 210, the image forming unit (image former) 220, and the data processor 230, as shown in FIG. 3.

(Controller 210)

The controller 210 controls each part of the ophthalmologic apparatus 1. The controller 210 includes a processor, a RAM, a ROM, a hard disk drive, and the like. The functions of the controller 210 are realized by the cooperation of hardware including circuits, and control software. The controller 210 includes a main controller 211 and a storage unit 212.

(Main Controller 211)

The main controller 211 executes various controls. In particular, the main controller 211 controls components of the fundus camera unit 2 such as a focusing drivers 31A and 43A, the CCD image sensors 35 and 38, the LCD 39, the optical path length changing unit 41, and the optical scanner 42. Further, the main controller 211 controls components of the OCT unit 100 such as the light source unit 101, the reference driver 114A, the detector 125, and the DAQ 130. In addition, the main controller 211 controls an optical system driver (not shown) for driving the optical systems shown in FIGS. 1 and 2.

The focusing driver 31A moves the imaging focusing lens 31 along an optical axis of the imaging optical system 30 under the control of the main controller 211. The focusing driver 31A is provided with a holding member that holds the imaging focusing lens 31, an actuator that generates a driving force for moving the holding member, and a transmission mechanism that transmits the driving force from the actuator to the holding member. The actuator includes a pulse motor, for example. The transmission mechanism includes a combination of gears, a rack and pinion, and the like, for example. As a result, the focusing driver 31A controlled by the main controller 211 moves the imaging focusing lens 31, thereby the focus position of the imaging optical system 30 is changed. Note that the focusing driver 31A may be configured to move the imaging focusing lens 31 along the optical axis of the imaging optical system 30 in accordance with a manual operation or the user's operation on an operation unit 242.

The focusing driver 43A moves an OCT focusing lens 43 along the optical axis of the interference optical system (the optical path of the measurement light) in the OCT unit 100 under the control of the main controller 211. The focusing driver 43A is provided with a holding member that holds the OCT focusing lens 43, an actuator that generates a driving force for moving the holding member, and a transmission mechanism that transmits the driving force from the actuator to the holding member. The actuator includes a pulse motor, for example. The transmission mechanism includes a combination of gears, a rack and pinion, and the like, for example. As a result, the focusing driver 43A controlled by the main controller 211 moves the OCT focusing lens 43, thereby the focus position of the measurement light is changed. Note that the focusing driver 43A may be configured to move the OCT focusing lens 43 along the optical axis of the interference optical system in accordance with a manual operation or the user's operation on the operation unit 242.

The main controller 211 can control an exposure time (charge accumulation time), a sensitivity, a frame rate, or the like of the CCD image sensor 35. The main controller 211 can control an exposure time, a sensitivity, a frame rate, or the like of the CCD image sensor 38.

The main controller 211 can control the LCD 39 to display fixation targets or visual targets for the visual acuity measurement. Thereby, the visual target presented to the subject's eye E can be switched, or type of the visual targets can be changed. Further, the presentation position of the visual target to the subject's eye E can be changed by changing the display position of the visual target on the screen of the LCD 39.

The main controller 211 can control the optical path length changing unit 41 to change relatively the difference between the optical path length of the reference light LR and the optical path length of the measurement light LS. The main controller 211 controls the optical path length changing unit 41 so as to render a target site of the subject's eye E in a predetermined range in the frame of an OCT image. Specifically, the main controller 211 can control the optical path length changing unit 41 so as to render the target site of the subject's eye E in a predetermined z position (a position in the depth direction) in the frame of the OCT image.

The main controller 211 can control the optical scanner 42 to change a scanning position of the measurement light LS on the fundus Ef or the anterior segment of the subject's eye E. Examples of the control of the optical scanner 42 include control of the galvano mirror that deflects the measurement light LS in the x direction and control of the galvano mirror that deflects the measurement light LS in the y direction. Examples of the control of the galvano mirror that deflects the measurement light LS in the x direction include the control of the scanning position, the scan range, or the scanning speed. Examples of the control of the galvano mirror that deflects the measurement light LS in the y direction include the control of the scanning position, the scan range, or the scanning speed. Further, the main controller 211 can control the scan mode of the measurement light LS using the optical scanner 42. Examples of scan mode of the measurement light LS using the optical scanner 42 include horizontal scan, vertical scan, cross scan, radial scan, circle scan, concentric scan, and helical (spiral) scan.

The main controller 211 can control the light source unit 101 to switch between lighting and non-lighting and to change light amount of the light LO, and the like.

The main controller 211 can control the reference driver 114A to change relatively the difference between the optical path length of the reference light LR and the optical path length of the measurement light LS. The reference driver 114A moves the corner cube 114 provided in the reference optical path. As a result, the length of the reference optical path is changed. The main controller 211 controls the reference driver 114A so as to render a target site of the subject's eye E in a predetermined range in the frame of an OCT image. Specifically, the main controller 211 can control the reference driver 114A so as to render the target site of the subject's eye E in a predetermined z position in the frame of the OCT image. The main controller 211 can change relatively the difference between the optical path length of the reference light LR and the optical path length of the measurement light LS, by controlling at least one of the optical path length changing unit 41 and the reference driver 114A. Hereinafter, a case will be described where the main controller 211 controls merely the optical path length changing unit 41 to adjust the difference of the optical path length between the measurement light LS and the reference light LR. However, the main controller 211 may control merely the reference driver 114A to adjust the difference of the optical path length between the measurement light LS and the reference light LR.

The main controller 211 can control an exposure time (charge accumulation time), a sensitivity, a frame rate, or the like of the detector 125. Further, the main controller 211 can control the DAQ 130.

The optical system driver (not shown) moves the optical system (the optical system shown in FIGS. 1 and 2) included in the ophthalmologic apparatus 1 three-dimensionally. The main controller 211 can control the optical system driver so as to maintain the positional relationship between the subject's eye E and the optical system of the apparatus. This control is used for alignment and/or tracking. Here, tracking is to move the optical system of the apparatus according to the movement of the subject's eye E. To perform tracking, alignment and focusing are performed in advance. The tracking is performed by moving the optical system of the apparatus in real time according to the position and orientation of the subject's eye E based on the image obtained by moving imaging the subject's eye E, thereby maintaining a suitable positional relationship in which alignment and focusing are adjusted.

(Storage Unit 212)

The storage unit 212 stores various types of data. Examples of the data stored in the storage unit 212 include image data of an OCT image, image data of a fundus image, and subject's eye information. The subject's eye information includes subject information such as patient ID and name, identification information of the left eye/right eye, and information of electronic medical record.

(Image Forming Unit 220)

The image forming unit 220 forms image data of a tomographic image of the fundus Ef and image data of a phase image of the fundus Ef based on detection signals from the detector 125 sampled by the DAQ 130. The image forming unit 220 includes a processor. It should be noted that "image data" and an "image" based on the image data may not be distinguished from each other in the present specification.

As shown in FIG. 4 the image forming unit (image former) 220 includes a tomographic image forming unit (tomographic image former) 221 and a phase image forming unit (phase image former) 222.

For example, as disclosed in Japanese Unexamined Patent Application Publication No. 2017-79886, in the embodiments, a scan for setting a target site for blood flow measurement (preliminary measurement) and a scan for acquiring blood flow information on the set site from the results of the preliminary measurement (blood flow measurement) are performed.

In the preliminary measurement, a plurality of cross sections of the fundus Ef are repeatedly scanned with the measurement light LS. The scan for the plurality of cross sections is a raster scan along a plurality of scan lines which are parallel to each other, for example. The number of scan lines in the raster scan is 128, for example. Thereby, a three-dimensional region of the fundus Ef is scanned (three-dimensional scan). Note that the scan pattern and the number of scan lines are not limited to the present example.

In the blood flow measurement, two types of scans (first scan and second scan) are performed based on the site of the fundus Ef set from the results of the preliminary measurement. The site set from the results of the preliminary measurement is referred to as the interested site. The interested site includes an interested blood vessel and an interested cross section. The interested blood vessel is a blood vessel of the fundus Ef set from the result(s) of the preliminary measurement. The interested blood vessel may be a blood vessel in which a pulse wave is clearly observed. The interested blood vessel may be an artery, for example. The interested cross section is a cross section intersecting the interested blood vessel. Further, the interested site may include one or more cross sections located in the vicinity of the interested cross section. The one or more cross sections are subject to OCT scan for obtaining the gradient of the interested blood vessel.

In the first scan, two or more cross sections intersecting the interested blood vessel of are scanned with the measurement light LS. The data acquired by performing the first scan is used to obtain the gradient (i.e., orientation) of the interested blood vessel at the interested cross section. Meanwhile, in the second scan, the interested cross section intersecting the interested blood vessel is repetitively scanned with the measurement light LS. The cross sections on which the first scan are performed are set near the interested cross section. The second scan is Doppler measurement using OCT.

Figure 8:
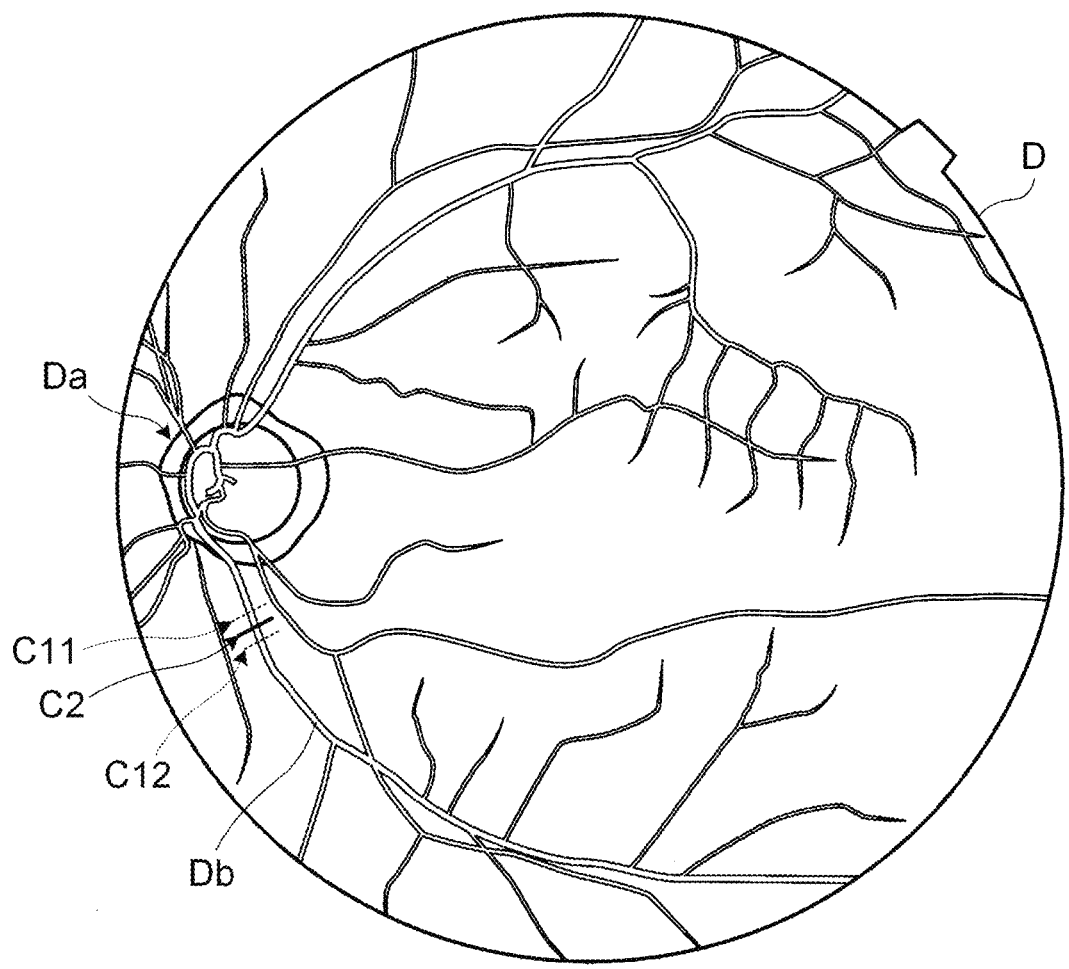
FIG. 8 is a schematic diagram for explaining an operation of the blood flow analysis apparatus according to the embodiments.

It may be desirable that the cross sections to be scanned in the first scan and the cross section to be scanned in the second scan are oriented, in the xy-plane, in such a manner that they are orthogonal to the running direction of the interested blood vessel. As shown in the fundus image D of FIG. 8, in the embodiments, for example, the two cross sections C11 and C12 where the first scan is to be performed and the interested cross section C2 where the second scan is to be performed are set, in the vicinity of the optic disc Da, so as to intersect with the interested blood vessel Db. One of the two cross sections C11 and C12 is located on the upstream side of the interested blood vessel Db with respect to the interested cross section C2, and another is located on the downstream side. The distance between the cross sections C11 and C12 with respect to the interested cross section C2 (inter-sectional distance) is determined in advance.

It may be desirable that the second scan is performed during a period equal to or longer than one heartbeat (i.e., one pulsation cycle, or cardiac cycle) of the heart of the subject. With this, blood flow information is acquired for all time phases of the cardiac cycle. The time for performing the second scan may be a preset period with a constant length (for example, 2 seconds), or may be set for each subject or each examination. In one of the latter cases, the heart rate data of the subject obtained using an electrocardiograph can be used.

(Tomographic Image Forming Unit 221)

The tomographic image forming unit 221 forms image data of a tomographic image (cross sectional image) of the fundus Ef based on the sampling result of the detection signals obtained by DAQ 130. The tomographic image forming unit 221 can form the tomographic image based on data acquired in the preliminary measurement. Further, the tomographic image forming unit 221 can form the tomographic image based on data acquired in the blood measurement (first scan and/or second scan). For example, the tomographic image forming unit 221 forms a tomographic image representing morphology in the cross section C11 and a tomographic image representing morphology in the cross section C12 based on detection results of the interference light LC acquired through the first scan on the cross sections C11 and C12. At this time, the cross section C11 may be scanned once and a single tomographic image may be formed, and the cross section C12 may be scanned once and a single tomographic image may be formed. Alternatively, a single tomographic image may be acquired based on a plurality of tomographic images obtained by scanning the cross section C11 a plurality of times, and a single tomographic image may be acquired based on a plurality of tomographic images obtained by scanning the cross section C12 a plurality of times. Examples of process for acquiring the single tomographic image from the plurality of tomographic images include a process for improving the image quality by averaging the plurality of tomographic images and a process for selecting the best one from the plurality of cross sectional images.

The tomographic image forming unit 221 forms a tomographic image group that represents the time-dependent change (time-course changes) in morphology in the interested cross section C2 based on the detection results of the interference light LC acquired through the second scan on the interested cross section C2. This process will be described in more detail. In the second scan, the interested cross section C2 is repeatedly scanned as described above. During the second scan, detection signals are successively transmitted from the detector 125 of the OCT unit 100 to the tomographic image forming unit 221. Based on the detection signal group corresponding to a single scan of the interested cross section C2, the tomographic image forming unit 221 forms a single tomographic image of the interested cross section C2. The tomographic image forming unit 221 repeats this process as many times as the number of repetition of the second scan, thereby forming a series of tomographic images arranged in time series order. The tomographic image forming unit 221 may divide these tomographic images into a plurality of groups and averages tomographic images in each group to improve image quality.

Processing performed by the tomographic image forming unit 221 includes noise elimination (noise reduction), filtering, fast Fourier transform (FFT), and the like as in conventional spectral domain OCT techniques. When other type of OCT is applied, the tomographic image forming unit 221 performs known processing according to the type of OCT.

(Phase Image Forming Unit 222)

The phase image forming unit 222 forms a phase image based on data (OCT data) acquired by repeatedly performing OCT scan on a predetermined site of the fundus Ef. Based on the data acquired through the preliminary measurement, the phase image forming unit 222 forms a phase image representing the time-dependent change in the phase difference at the scanned cross section. In the preliminary measurement, a plurality of cross sections of the fundus Ef are repeatedly scanned with the measurement light LS. The phase image forming unit 222 forms a phase image at each of these cross sections based on the data acquired through the preliminary measurement.

Further, the phase image forming unit 222 forms the phase image based on the data acquired through the second scan in the blood flow measurement. For example, the phase image forming unit 222 forms the phase image that represents the time-dependent change in phase difference in the interested cross section C2, based on detection results of the interference light LC acquired through the second scan on the interested cross section C2.

The data used for forming the phase image may be the same as that used for forming the tomographic image formed by the tomographic image forming unit 221. In this case, position matching between the phase image and the tomographic image of the scanned cross section can be easily performed. In other words, for the tomographic image and the phase image based on the same data, pixels in the tomographic image and those in the phase image can be associated with each other in a natural manner.

An example of the method of forming the phase images will be described. A phase image in the present example is obtained by calculating the phase differences between adjacent A-line complex signals (that is, signals corresponding to adjacent scan points). In other words, a phase image in the present example is formed based on time-dependent change in the pixel value (brightness value) of each pixel in the tomographic image of the scanned cross section. For any pixel, the phase image forming unit 222 takes account of a graph representing the time-dependent change in the brightness value of the concerned pixel. The phase image forming unit 222 obtains the phase difference $\Delta\varphi$ between two time points t1 and t2 that are apart from each other by a preset time interval $\Delta t$ in the graph. Here, $t2 = t1 + \Delta t$. The phase difference $\Delta\varphi$ is defined as the phase difference $\Delta\varphi$ at the time point t1. More generally, the phase difference $\Delta\varphi$ may be defined as the phase difference at any time point between the two time points t1 and t2 (including t1 and t2). By executing such processing for each of a plurality of time points set in advance, the time-dependent change in the phase difference at the concerning pixel can be obtained.

The phase image is formed by representing, as an image, the values of the phase differences at time points for pixels. Such imaging processing can be realized by representing the values of the phase differences with colors or brightness, for example. At this time, it is possible to differentiate the color indicating that the phase has increased with the lapse of time and the color indicating that the phase has decreased. For example, red is assigned to the former case while blue is assigned to the latter case. It is also possible to represent the magnitude of the phase change amount with the density of display color. With such representation methods, the direction and/or magnitude of blood flow can be represented with colors and/or density. The processing described above is applied to each pixel to form the phase image.

The time interval $\Delta t$ described above can be set sufficiently small to secure phase correlation. This allows to obtain the time-dependent change in phase difference. Here, oversampling is performed in which the time interval $\Delta t$ is set to be a value smaller than the period corresponding to the resolution of tomographic images in the scan with the measurement light LS.

(Data Processor 230)

The data processor 230 performs various kinds of data processing (e.g., image processing) and various kinds of analysis processing on an image formed by the image forming unit 220. For example, the data processor 230 performs various correction processes such as brightness correction and dispersion correction of images. Further, the data processor 230 performs various types of image processing and analysis processing on images (anterior segment image, etc.) acquired using the CCD image sensors 35 and 38.

The data processor 230 can form volume data (voxel data) of the subject's eye E by performing known image processing such as interpolation processing for interpolating pixels between cross sectional images. In the case of displaying an image based on the volume data, the data processor 230 performs rendering processing on the volume data so as to form a pseudo three-dimensional image viewed from a specific line-of-sight direction.

The data processor 230 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired volume data (three-dimensional data set, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

Further, the data processor 230 can build (form) the B-mode image or the front image (blood vessel emphasized image, angiogram) in which retinal blood vessels and choroidal blood vessels are emphasized (highlighted), based on data (for example, B scan image data) acquired in time series by OCT. For example, the OCT data in time series can be acquired by repeatedly scanning substantially the same site of the subject's eye E.

In some embodiments, the data processor 230 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 230 forms an OCT angiogram by extracting information of a predetermined thickness at a desired site from a plurality of built emphasized images and building as an en-face image.

Further, the data processor 230 can specify a predetermined layer region in the tomographic image formed by the image forming unit 220. Examples of the specifiable layer region include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, the choroid, the sclera, the boundary surfaces of each layer region, and the like.

Processing of specifying the predetermined layer region from the tomographic image typically includes segmentation processing. The segmentation processing is known processing for specifying a partial region in a tomographic image. The data processor 230 performs, for example, segmentation processing based on a brightness value of each pixel in the tomographic image. That is, each of the layer regions of the fundus Ef has a characteristic reflectance, and image regions corresponding to these layer regions also have characteristic brightness values. The data processor 230 can specify a target image region (layer region) by performing segmentation processing based on these characteristic brightness values. The data processor 230 specifies a layer region where at least a retinal artery or a retinal vein is present (e.g., layer region between inner limiting membrane and Bruch membrane). In some embodiments, the data processor 230 specifies an image region in the phase image corresponding to the layer region specified in the tomographic image.

The data processor 230 can generate blood flow information based on image (tomographic image, phase image) formed by the image forming unit 220. Specifically, the data processor 230 generates the blood flow information on a predetermined layer region (e.g., layer region between inner limiting membrane and Bruch membrane) specified, as described above, in the image (tomographic image, phase image) formed by the image forming unit 220. Further, the data processor 230 can analyze the generated blood flow information to extract one or more parameters, and can evaluate the dynamics of general circulation of the subject based on the extracted one or more parameters. Such the data processor 230 includes, as shown in FIG. 5, a blood flow information generation processor 231 and a blood flow information analysis processor 232.

(Blood Flow Information Generation Processor 231)

The blood flow information generation processor 231 performs processing on the data acquired in the blood flow measurement for the site set based on the preliminary measurement. In the present example, the blood flow information generation processor 231 obtains a gradient of the interested blood vessel in the interested cross section, based on the data acquired through the first scan for a single blood vessel. Further, the blood flow information generation processor 231 obtains the blood flow information on the interested blood vessel based on the gradient of the interested blood vessel obtained based on the first scan and the data acquired through the second scan. The blood flow information includes a blood flow velocity and a blood flow amount, for example. Such the blood flow information generation processor 231 includes a blood vessel region specifying unit (blood vessel region specifier) 2311, a gradient calculator 2312, a blood flow velocity calculator 2313, a blood vessel diameter calculator 2314, and a blood flow amount calculator 2315, as shown in FIG. 6.

(Blood Vessel Region Specifying Unit 2311)

The blood vessel region specifying unit 2311 specifies a blood vessel region corresponding to the interested blood vessel in the tomographic image formed by the tomographic image forming unit 221. In addition, the blood vessel region specifying unit 2311 specifies a blood vessel region corresponding to the interested blood vessel in the phase image formed by the phase image forming unit 222. The specification of the blood vessel region is performed by analyzing the pixel values of each image (for example, threshold processing). In some embodiments, the blood vessel region specifying unit 2311 specifies the blood vessel region by performing threshold processing, edge detection, binarization, thinning processing, and region expansion method (region drawing) on the tomographic image or the phase image.

In some embodiments, when the shape of the blood vessel region depicted in the phase image is substantially circular, the blood vessel region specifying unit 2311 specifies the blood vessel region by specifying a substantially circular region having a large change in brightness difference or phase difference.

In the embodiments, the tomographic image and the phase image can be formed from the same data. Thereby, the blood vessel region specifying unit 2311 can specify the blood vessel region in the tomographic image, in which the morphology of the cross section is depicted relatively clearly, and can specify the region in the phase image corresponding to the blood vessel specified in the tomographic image. Further, even when the tomographic image and the phase image are formed from the different data, if their registration is possible directly or indirectly, the results of specifying the blood vessel region in one image can be used to specify the blood vessel region in another image.

In some embodiments, the blood vessel region specifying unit 2311 specifies the blood vessel region specified based on the operation content performed by the user on the operation unit 242 (described later). The user can specify the blood vessel region corresponding to a desired interested blood vessel, by performing operations on the operation unit 242 while watching the front image of the fundus Ef or the phase image of the cross section of the fundus Ef displayed on the display unit 241 (described later) by the main controller 211.

(Gradient Calculator 2312)

The gradient calculator 2312 calculates the gradient of the interested blood vessel Db at the interested cross section C2 based on the data acquired through the first scan. At this time, it is also possible to further use the data acquired through the second scan. The gradient calculator 2312 calculates the gradient of the interested blood vessel Db at the interested cross section C2 based on the specification results of the blood vessel region and a cross section interval. The cross section interval may include a distance between the cross section C11 and the cross section C12. Alternatively, the cross section interval may include a distance between the cross section C11 and the interested cross section C2 and a distance between the cross section C12 and the interested cross section C2.

Figure 9:
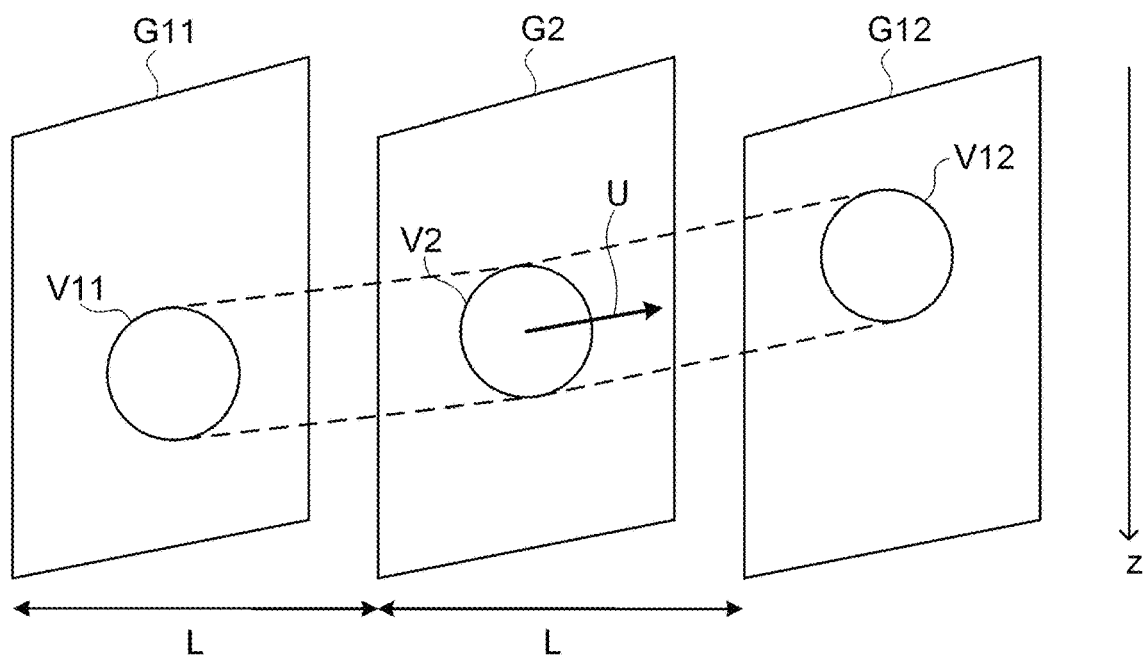
FIG. 9 is a schematic diagram for explaining an operation of the blood flow analysis apparatus according to the embodiments.

A method of calculating the gradient of the interested blood vessel Db will be described with referring to FIG. 9. Tomographic images G11 and G12 are the tomographic images representing the cross sections C11 and C12 to which the first scan is to be applied, respectively. Further, the tomographic image G2 is a tomographic image representing the interested cross section C2 to which the second scan is to be applied. The sign V11 indicates the blood vessel region in the tomographic image G11. The sign V12 indicates the blood vessel region in the tomographic image G12. The sign V2 indicates the blood vessel region in the tomographic image G2. It should be noted that these blood vessel regions correspond to cross sections of the interested blood vessel Db. In FIG. 9, the z coordinate axis is oriented downward, and substantially coincides with the projection direction of the measurement light LS (i.e., the direction the optical axis of the optical path of the measurement light LS, axis direction, A-line direction). The interval between adjacent tomographic images (i.e., cross sections) is represented by L.

In one example, the gradient calculator 2312 calculates the gradient "U" of the interested blood vessel Db at the interested cross section C2 based on the positional relationship between the three blood vessel regions V11, V12 and V2. This positional relationship is obtained, for example, by connecting the three blood vessel regions V11, V12 and V2. Specifically, the gradient calculator 2312 specifies the characteristic points of each of the three blood vessel regions V11, V12, and V2, and connects these characteristics points. The characteristic point may be the center position, the position of the center of gravity, the highest position (the position corresponding to the smallest z coordinate value), the lowest position (the position corresponding to the largest z coordinate value), or the like. Further, examples of the method of connecting these characteristic points include a method of connecting with line segments and a method of connecting with approximate curves (spline curves, Bezier curves, etc.).

Further, the gradient calculator 2312 calculates the gradient "U" based on the line connecting these characteristic points. When line segments are used, for example, the gradient "U" is calculated based on the gradient of a first line segment connecting the characteristic point of the blood vessel region V2 in the interested cross section C2 with the characteristic point of the blood vessel region V11 in the interested cross section C11, and the gradient of a second line segment connecting the characteristic point of the blood vessel region V2 with the characteristic point of the blood vessel region V12 in the cross section C12. As an example of this calculation process, the average value of the gradients of the two line segments can be obtained. Alternatively, as an example of connecting with the approximate curve, the gradient of the approximate curve at an intersection of the approximate curve and the interested cross section C2 can be obtained. Note that the cross section interval L is used to embed the tomographic images G11, G12, and G2 in the xyz coordinate system in the process of obtaining the line segment or the approximate curve.

In the present example, the blood vessel regions in the three cross sections are considered. However, the gradient may be obtained by considering the blood vessel regions at the two cross sections. As a specific example, the gradient "U" of the interested blood vessel Db at the interested cross section C2 can be configured to be obtained based on the blood vessel region V11 in the cross section C11 and the blood vessel region V12 in the cross section C12. Alternatively, the gradient of the first line segment described above or the gradient of the second line segment described above can be used as the gradient "U".

The method of calculating the gradient of the interested blood vessel at the interested cross section is not limited to the method(s) described above. For example, the following method may be applied. First, an OCT scan is performed on the cross section that intersects the interested cross section and follows the interested blood vessel. Next, a tomographic image is formed based on data acquired through this OCT scan. And then, the segmentation is performed on this tomographic image to specify an image region (layer region) corresponding to a predetermined tissue. The layer region to be specified is, for example, a layer region corresponding to the inner limiting membrane (ILM region). The inner limiting membrane is a tissue in the retina that defines the boundary between the retina and the vitreous and is relatively clearly depicted. Further, the line segment that approximates the shape of the specified layer region is obtained. And then, the gradient of the line segment is obtained. The gradient of the approximate line segment is represented, for example, as an angle with respect to the z-coordinate axis or an angle with respect to the xy-plane (i.e., a plane orthogonal to the z-coordinate axis).

(Blood Flow Velocity Calculator 2313)

Based on the time-dependent change in the phase difference obtained as the phase image, the blood flow velocity calculator 2313 calculates a blood flow velocity at the interested cross section C2 for the blood flowing through the interested blood vessel Db. The target to be calculated may be the blood flow velocity at a certain time point or may be the time-dependent change in the blood flow velocity. The time-dependent change in the blood flow velocity is referred to as blood flow velocity variation information. When the blood flow velocity at a certain time point is obtained, the blood flow velocity at a predetermined time phase in an electro cardiogram (e.g., time phase corresponding to the R wave) may be selectively acquired, for example. When the time-dependent change in the blood flow velocity is obtained, the measurement period is the whole or an arbitrary part of the period taken for the scan of the interested cross section C2.

When the blood flow velocity variation information is acquired, the blood flow velocity calculator 2313 can further calculate a statistic of the blood flow velocity in the measurement period. Examples of the statistic include the mean value, the standard deviation, the variance, the median, the global maximum, the global minimum, the local maximum, and the local minimum. The blood flow velocity calculator 2313 can also create a histogram on the blood flow velocity values.

The blood flow velocity calculator 2313 calculates the blood flow velocity using Doppler OCT technique as described above. In the blood flow velocity calculation, the gradient "U" of the interested blood vessel Db at the interested cross section C2 calculated by the gradient calculator 2312 is taken into account. Specifically, the gradient calculator 2312 applies the following equation to the blood flow velocity calculation.

[Equation 1]

$$\Delta f = \frac{2nv \cdot \cos\theta}{\lambda} \quad (1)$$

In equation (1), $\Delta f$ represents the Doppler shift that the scattered light of the measurement light LS receives, "n" represents the refractive index of the medium (blood), "v" represents the flow velocity of the medium (blood flow velocity), "θ" represents the angle formed between the direction of incidence of the measurement light LS and the direction of flow of the medium (gradient "U"), and "λ" represents the central wavelength of the measurement light LS.

In the embodiments, "n" and "k" are known, "Δf" is obtained from the chronological change of the phase difference, and "θ" is obtained from the gradient "U" (or "θ" is obtained as the gradient "U"). The blood flow velocity "v" is calculated by substituting these values into the equation (1).

(Blood Vessel Diameter Calculator 2314)

The blood vessel diameter calculator 2314 calculates the diameter of the interested blood vessel Db at the interested cross section C2, by analyzing the fundus image or the OCT image. When the fundus image is used, the site including the position of the interested cross section C2 of the fundus Ef is photographed. And then, a diameter of the interested blood vessel Db at the interested cross section C2 (i.e., a diameter of the blood vessel region V2) is calculated based on the fundus image (e.g., color fundus image, red-free image, etc.) obtained by photographing. When the OCT image is used, this OCT image is, for example, a tomographic image formed based on the second scan or an image formed based on the preliminary measurement. Such calculation of the blood vessel diameter is performed in the same manner as before.

(Blood Flow Amount Calculator 2315)

Based on the calculation result of the blood flow velocity and the calculation result of the blood vessel diameter, the blood flow amount calculator 2315 calculates the flow amount (or, flow volume or flow rate) of the blood that flows through the interested blood vessel Db. An example of the calculation process will be described below.

It is assumed that the blood flow in a blood vessel is the Hagen-Poiseuille flow. The blood vessel diameter is denoted by "w", and the maximum blood flow velocity is denoted by "Vm". Then, the blood flow amount "Q" is given by the following equation.

[Equation 2]

$$Q = \frac{\pi w^2}{8} Vm \quad (2)$$

The blood flow amount calculator 2315 substitutes the calculation result "w" of the blood vessel diameter calculated by the blood vessel diameter calculator 2314 and the maximum "Vm" based on the calculation result of the blood flow velocity calculated by the blood flow velocity calculator 2313 into the equation (2) to obtain the blood flow amount "Q".

(Blood Flow Information Analysis Processor 232)

The blood flow information analysis processor 232 performs analysis processing on the blood flow information generated by the blood flow information generation processor 231. In the present example, the blood flow information analysis processor 232 acquires blood flow information representing time-course changes in blood flow velocity of a single retinal artery or a single retinal vein from the blood flow information generated by the blood flow information generation processor 231, and extracts one or more parameters corresponding to the change in the blood flow velocity of the subject's eye from the acquired blood flow information. In some embodiments, the blood flow information analysis processor 232 evaluates the extracted one or more parameters. Such the blood flow information analysis processor 232 includes, as shown in FIG. 7, an extractor 2321 and a parameter evaluation unit 2322.

(Extractor 2321)

The extractor 2321 extracts predetermined one or more parameters from the blood flow information generated by the blood flow information generation processor 231. The extractor 2321 specifies the blood flow velocity variation information (in a broader sense, blood flow information) representing time-course changes in the blood flow velocity from the blood flow information generated by the blood flow information generation processor 231, and extracts the one or more parameters, which are described above, from the specified blood flow velocity variation information. Such the extractor 2321 includes, as shown in FIG. 7, a cardiac cycle specifying unit 2321A, a normalization unit 2321B, and an interpolation unit 2321C.

(Cardiac Cycle Specifying Unit 2321A)

The cardiac cycle specifying unit 2321A specifies a cardiac cycle from the blood flow velocity variation information representing the time-course changes in the blood flow velocity. The time-course changes in the blood flow velocity are changes caused by the beating of the heart. The cardiac cycle specifying unit 2321A, for example, specifies the cardiac cycle by specifying the point of change in the blood flow velocity corresponding to the beating.

Figure 10:
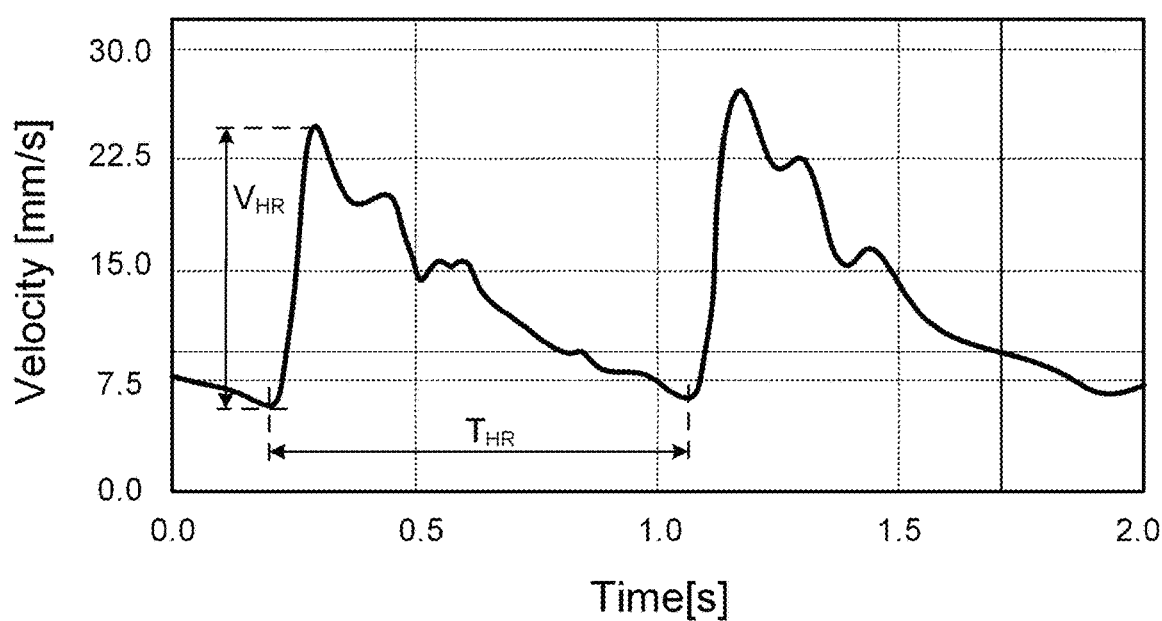
FIG. 10 is a schematic diagram for explaining an operation of the blood flow analysis apparatus according to the embodiments.

FIG. 10 shows a diagram for explaining the operation of the extractor 2321. FIG. 10 shows an example of a blood flow velocity waveform that represents the time-course changes in the blood flow velocity. In FIG. 10, the horizontal axis represents the time, while the vertical axis represents the blood flow velocity.

The cardiac cycle specifying unit 2321A specifies the period between the two timings when the blood flow velocity becomes a predetermined value from the blood flow velocity variation information, as the cardiac cycle $T_{HR}$ required for one heartbeat. Examples of the predetermined value include the local minimum, the local maximum, the global minimum, and the global maximum. In the embodiments, the cardiac cycle specifying unit 2321A specifies the period between the two timings when the blood flow velocity becomes the global minimum as the cardiac cycle $T_{HR}$ one heartbeat. The cardiac cycle specifying unit 2321A may output the statistic of two or more cardiac cycles specified from the blood flow velocity variation information as the cardiac cycle $T_{HR}$. Examples of the statistic include the mean value, the standard deviation, the variance, the median, the global maximum, the global minimum, the local maximum, and the local minimum.

(Normalization Unit 2321B)

The normalization unit 2321B normalizes the blood flow velocity variation information between the cardiac cycle $T_{HR}$ specified by the cardiac cycle specifying unit 2321A. Specifically, the normalization unit 2321B normalizes the blood flow velocity variation information in the time axis direction (horizontal axis direction) and in the blood flow velocity axis direction (vertical axis direction) based on the cardiac cycle $T_{HR}$. The normalization in the time axial direction corresponds to the normalization of the cardiac cycle. The normalization in the blood flow velocity axis direction corresponds to the normalization of the amplitude of the blood flow velocity.

The normalization unit 2321B normalizes the blood flow velocity variation information in the time axis direction so that the number of measurement samples of the blood flow velocity becomes a predetermined number of measurement samples within a predetermined time (e.g., 1 second or 2 seconds). Further, the normalization unit 2321B normalizes, as shown in FIG. 10, the blood flow velocity variation information in the blood flow velocity axis direction so that the maximum of the difference $V_{HR}$ between the global maximum and the global minimum of the blood flow velocity within the cardiac cycle $T_{HR}$ becomes "1" and the minimum of the difference $V_{HR}$ becomes "0".

In some embodiments, when the number of measurement samplings after normalization exceeds a predetermined number of measurement samplings, the normalization unit 2321B thins out one or more measurement sampling points. In some embodiments, when the number of measurement samplings after normalization is less than the predetermined number of measurement samplings, the interpolation unit 2321C described later adds one or more sampling points by interpolation.

(Interpolation Unit 2321C)

The interpolation unit 2321C adds one or more sampling points (blood flow velocity) by interpolation, when the number of samplings after normalization is less than the predetermined number of measurement samplings, as described above. In some embodiments, the one or more samplings are added using a known interpolation method such as spline interpolation.

In some embodiments, the interpolation processing performed by the interpolation unit 2321C is omitted for the blood flow velocity variation information normalized by the normalization unit 2321B. In some embodiments, the interpolation unit 2321C interpolates the blood flow velocity variation information and the normalization unit 2321B normalizes the blood flow velocity variation information interpolated by the interpolation unit 2321C in the time axis direction and in the blood flow velocity axis direction.

By performing such normalization and interpolation processes, parameters can be extracted from the blood flow velocity variation information of the same number of sampling points for subjects with different heart rates (cardiac cycles). Thereby, the accuracy of the parameters extracted from the subject's eye can be improved, and the accuracy of evaluation based on the parameter(s) can be improved.

The extractor 2321 extracts the one or more parameters from the blood flow velocity variation information generated by the cardiac cycle specifying unit 2321A, the normalization unit 2321B, and the interpolation unit 2321C. The one or more parameters include a time required from a reference timing to a characteristic point of the change in blood flow velocity within the cardiac cycle $T_{HR}$ or an area under the waveform thereof.

Figure 11A:
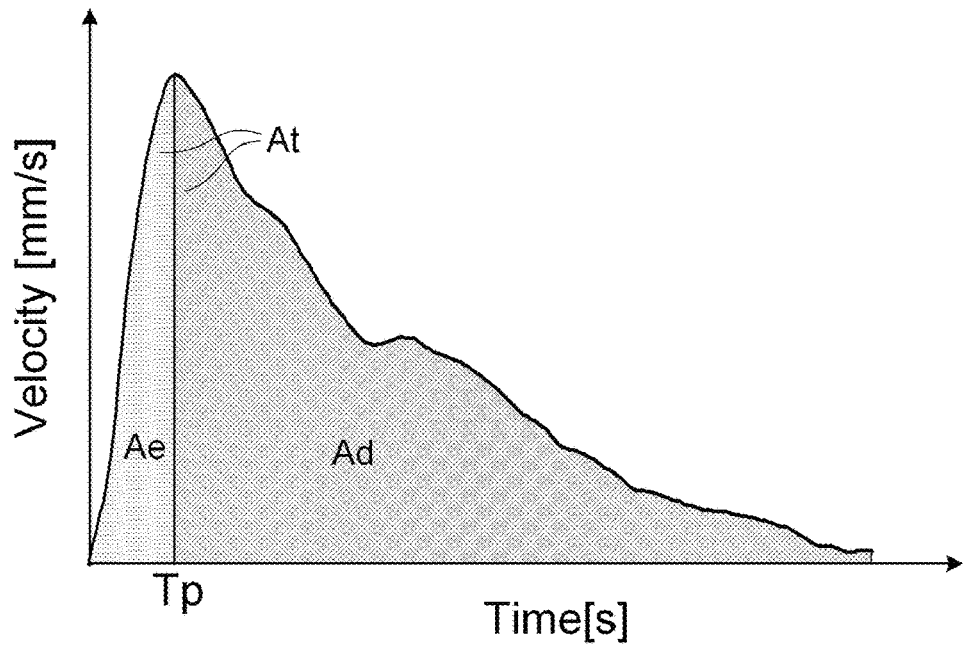
FIG. 11A is a schematic diagram for explaining an operation of the blood flow analysis apparatus according to the embodiments.
Figure 11B:
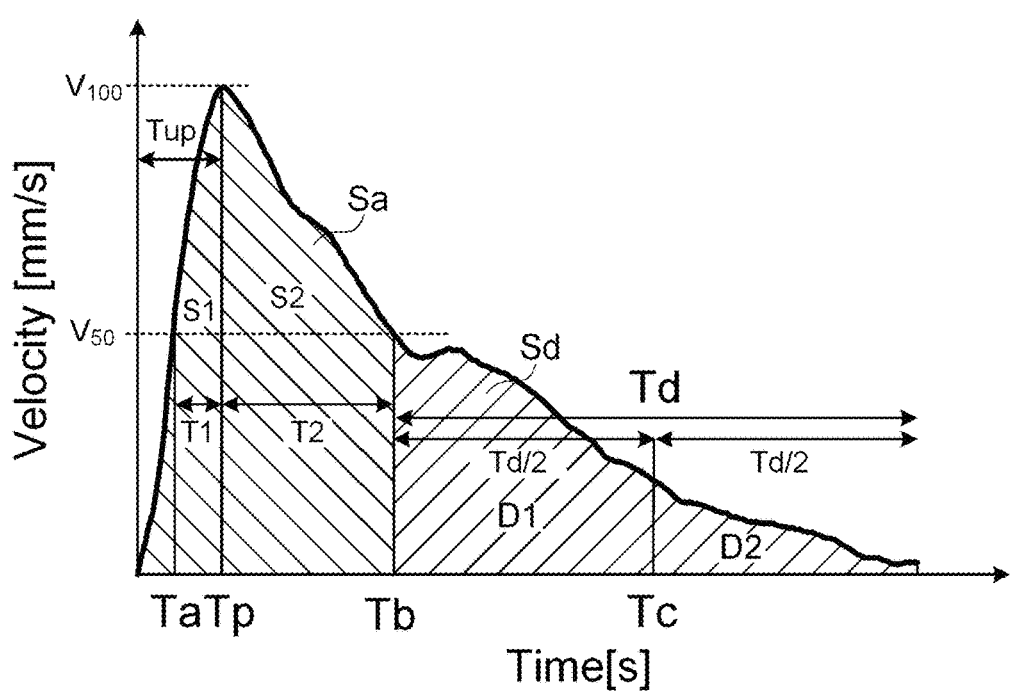
FIG. 11B is a schematic diagram for explaining an operation of the blood flow analysis apparatus according to the embodiments.

FIGS. 11A and 11B show diagrams explaining the one or more parameters according to the embodiments. In FIGS. 11A and 11B, the horizontal axis represents the time, while the vertical axis represents the blood flow velocity.

Examples of the parameter extracted by the extractor 2321 include an area total At, an area elevation Ae, and an area declination Ad (see FIG. 11A). Here, At=Ae+Ad. The area total At is an area under the waveform between the start timing (time) of the cardiac cycle $T_{HR}$ and the end timing of the cardiac cycle Tim. The area elevation Ae is an area under the waveform between the start timing of the cardiac cycle $T_{HR}$ and the peak arrival timing Tp of the blood flow velocity. The area declination Ad is an area under the waveform between the peak arrival timing TP of the blood flow velocity and the end timing of the cardiac cycle $T_{HR}$.

Further, examples of the parameter extracted by the extractor 2321 include an area systolic Sa, an area diastolic Sd, S1 part, S2 part, D1 part, and D2 part (see FIG. 11B). Here, At=Sa+Sd, Sa=S1+S2, and Sd=D1+D2. The area systolic Sa is an area under the waveform in a systolic phase within the cardiac cycle Tim. In the embodiments, the period from the start timing of the cardiac cycle $T_{HR}$ to the timing Tb is defined as the systolic phase. The timing Tb is a timing at which the blood flow velocity reaches $V_{50}$, which is half of the maximum value $V_{100}$ (peak arrival timing Tp) during the falling period of the blood flow velocity. The area diastolic Sd is an area under the waveform in a diastolic phase with in the cardiac cycle $T_{HR}$. This area under the waveform is an area under the waveform of the time-course changes in the blood flow velocity in the diastolic phase. In the embodiments, the period from the timing Tb to the end timing of the cardiac cycle $T_{HR}$ is defined as the diastolic phase. The S1 part is an area under the waveform from the start timing of the cardiac cycle $T_{HR}$ (systolic phase) to the peak arrival timing Tp. The S2 part is an area under the waveform from the peak arrival timing Tp of the cardiac cycle $T_{HR}$ (systolic phase) to the timing Tb. The D1 part is an area under the waveform from the timing Tb to the timing Tc within the cardiac cycle $T_{HR}$ (diastolic phase). This area under the waveform is an area under the waveform of the time-course changes in the blood flow velocity in the first half of the diastolic phase. When the period from the timing Tb to the end of the cardiac cycle $T_{HR}$ is Td, the timing Tc is a timing that elapses by Td/2 from timing Tb (Tc=Tb+Td/2). The D2 part is an area under the waveform from the timing Tc within the cardiac cycle $T_{HR}$ (diastolic phase) to the end timing of the cardiac cycle Tim. This area under the waveform is an area under the waveform of the time-course changes in the blood flow velocity in the second half of the diastolic phase. It should be noted that at least one of the timings Tb and Td may be changed arbitrarily.

Further, examples of the parameter extracted by the extractor 2321 include a half width ascending period T1, a half width descending period T2, and an upstroke time (width) Tup. The half width ascending period T1 is a time (first time) between the timing Ta and the peak arrival timing Tp. The timing Ta is a timing when the blood flow velocity reaches $V_{50}$ (first blood flow velocity) during the rising period of blood flow velocity (systolic phase). The half width descending period T2 is a time (second time) between the peak arrival timing Tp and the timing Tb. The timing Tp is a timing when the blood flow velocity reaches $V_{50}$ during the falling period of the blood flow velocity after the peak arrival timing. The upstroke time Tup is a time between the start timing of the cardiac cycle $T_{HR}$ and the peak arrival timing Tp of the blood flow velocity.

In some embodiments, the extractor 2321 obtains a new parameter using at least one of the area systolic Sa, the area diastolic Sd, the S1 part, the S2 part, the D1 part, and the D2 part. For example, the extractor 2321 obtains a ratio of the area systolic Sa or the area diastolic Sd to the area systolic Sa (or the area total At), a ratio of the area systolic Sa and the area diastolic Sd, a ratio of the S1 part or the S2 part to the area systolic Sa, a ratio of the S1 part and the S2 part, a ratio of the D1 part or the D2 part to the area diastolic Sd, a ratio of the D1 part and the D2 part, or the like.

In some embodiments, the extractor 2321 obtains a new parameter using at least one of the half width ascending period T1, the half width descending period T2, and the upstroke time Tup. For example, the extractor 2321 obtains a ratio of the half width ascending period T1 to the upstroke time Tup, a ratio of the half width ascending period T1 and the half width descending period T2, a ratio of the half width ascending period T1 or the half width descending period T2 to the sum of the half width ascending period T1 and the half width descending period T2 (T1/(T1+T2), or T2/(T1+T2)).

The method of extracting parameters by the extractor 2321 according to the embodiments is not limited to the above method. The extractor 2321 can extract one or more parameters using a known waveform processing method such as Fourier transform, differential method, peak detection, area calculation, moment calculation.

(Parameter Evaluation Unit 2322)

The parameter evaluation unit 2322 performs predetermined evaluation processing based on the one or more parameters extracted by the extractor 2321. For example, based on the time dependency of a predetermined evaluation item obtained by analyzing in advance a plurality of time-course changes in the blood flow velocities obtained by OCT measurements for a plurality of eyes of the subjects, the parameter evaluation unit 2322 performs an evaluation of the dynamics of the general circulation of the subject based on the one or more parameters extracted by the extractor 2321.

In some embodiments, the parameter evaluation unit 2322 evaluates whether or not the time-course changes in the blood flow velocity of the subject's eye are age-related changes caused by changes in circulatory dynamics due to aging. In some embodiments, the parameter evaluation unit 2322 evaluates the degree of the dynamics of the general circulation from the changes in the blood flow velocity of the subject's eye. Examples of the degree of the dynamics of the general circulation include an arteriosclerosis index, an index related to cardiac function.

For the analysis of a plurality of time-course changes in the blood flow velocities in advance, a known analysis method is used. Examples of known analysis method include regression analysis (single regression analysis, multiple regression analysis) and machine learning such as random forest and support vector machine. In this case, the parameter evaluation unit 2322 can acquire an evaluation result corresponding to the one or more parameters extracted by the extractor 2321, using the regression line or curve obtained by the regression analysis. Alternatively, the parameter evaluation unit 2322 can acquire an evaluation result corresponding to the one or more parameters extracted by the extractor 2321, using a trained model obtained by performing machine learning.

FIGS. 12 to 15 show the relationship between the age and the parameters extracted by the extractor 2321. FIGS. 12 to 15 represent the relationship between the age and the parameter. Here, the parameter is obtained from the results of OCT measurements under non-mydriatic conditions in 39 eyes of 39 subjects (male:female ratio, 21:18) aged 50.0±24.3 years. However, subjects with a history of ocular disease or cardiac disease or hypertension (systolic blood pressure of 140 or higher and/or diastolic blood pressure of 90 or higher) are excluded.

Figure 12:
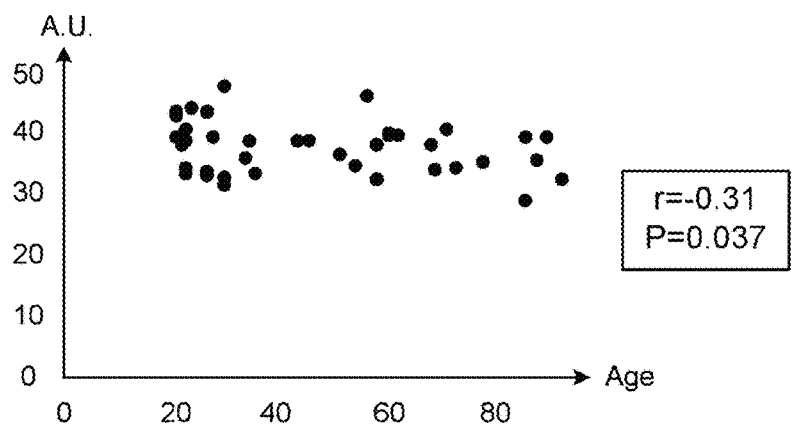
FIG. 12 is a schematic diagram for explaining an operation of the blood flow analysis apparatus according to the embodiments.
Figure 12:
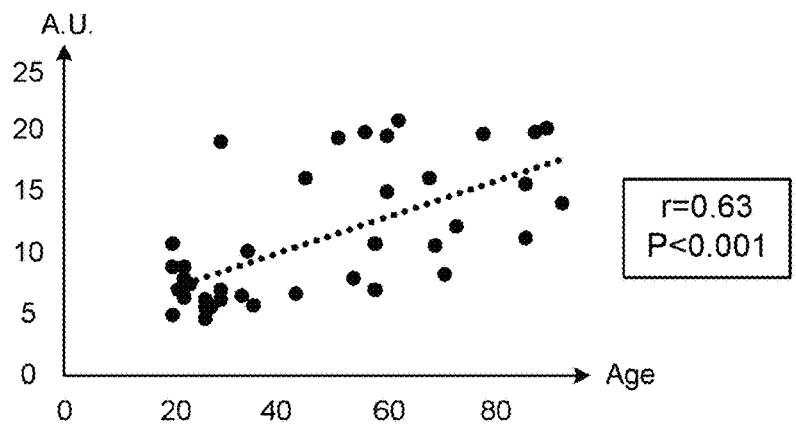
Figure 12:
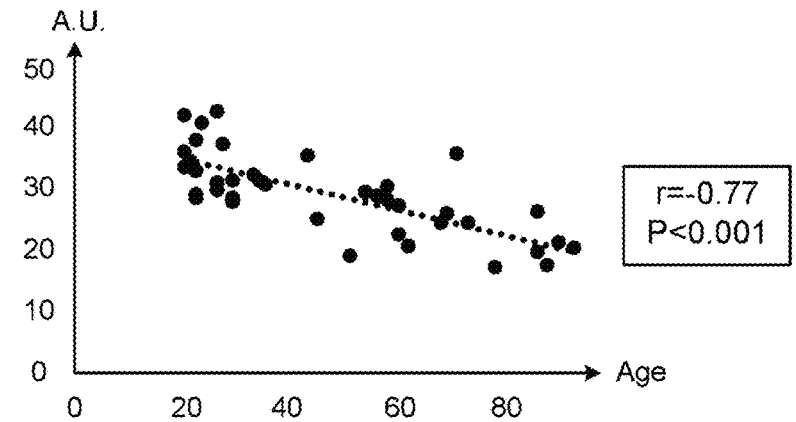

FIG. 12 shows (a) the correlation between the area total At and the age, (b) the correlation between the area elevation Ae and the age, and (c) the correlation between the area declination Ad and the age. In FIG. 12 (a) to (c), the horizontal axis represents the age, while the vertical axis represents arbitrary unit.

From the r values corresponding to the correlation coefficients and the P values corresponding to the significance probabilities in (a) to (c) of FIG. 12, at least the area elevation Ae has a positive correlation with the age, and the area declination Ad has a negative correlation with the age. For example, by specifying the regression line (regression curve) in a plurality of the area elevations Ae or a plurality of the area declinations Ad, it is possible to evaluate whether or not the change in the blood flow velocity of the subject's eye is an age-related change from the area elevation Ae or the area declination Ad extracted based on the time-course changes in the blood flow velocity of the subject's eye. Further, when the area elevation Ae or the area declination Ad is associated with an arteriosclerosis index (or an index related to cardiac function), it is possible to evaluate the degree of dynamics of the general circulation from the area elevation Ae or the area declination Ad extracted based on the time-course changes in the blood flow velocity of the subject's eye.

Figure 13:
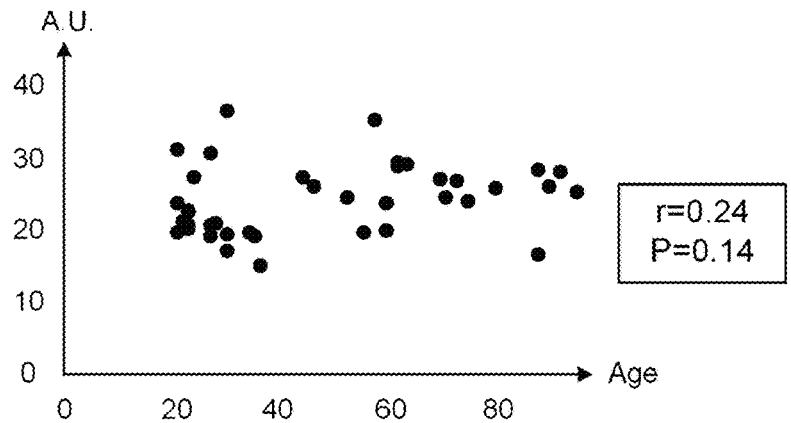
FIG. 13 is a schematic diagram for explaining an operation of the blood flow analysis apparatus according to the embodiments.
Figure 13:
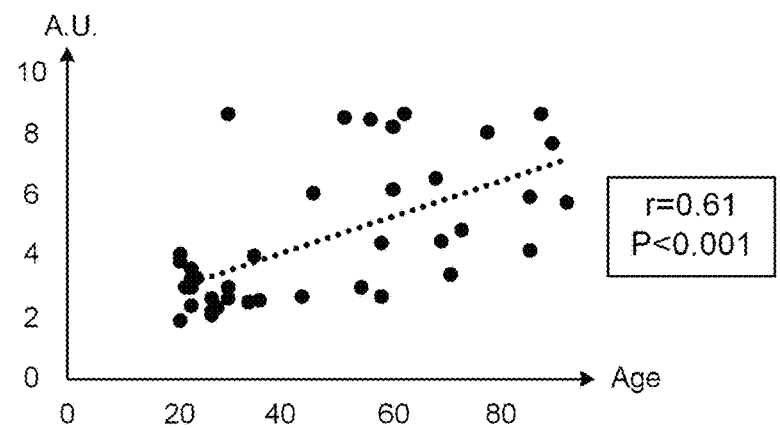
Figure 13:
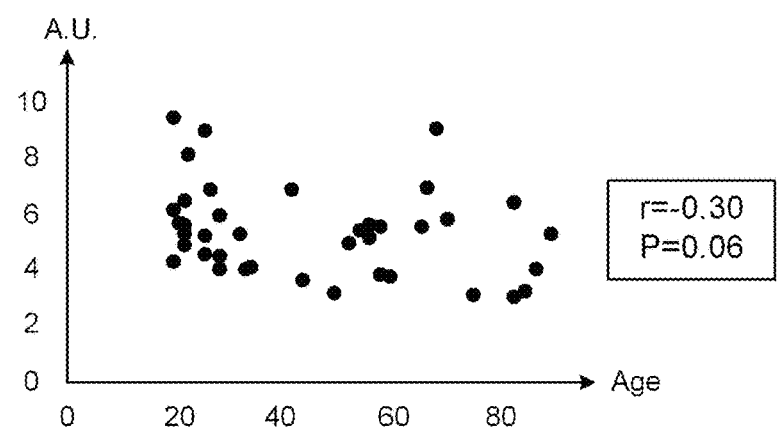

FIG. 13 shows (a) the correlation between the area systolic Sa and the age, (b) the correlation between the S1 part and the age, and (c) the correlation between the S2 part and the age. In FIG. 13 (a) to (c), the horizontal axis represents the age, while the vertical axis represents arbitrary unit.

From the r values and the P values in (a) to (c) of FIG. 13, at least the S1 part a positive correlation with the age. For example, by specifying the regression line (regression curve) in a plurality of the S1 parts, it is possible to evaluate whether or not the change in the blood flow velocity of the subject's eye is an age-related change from the S1 part extracted based on the time-course changes in the blood flow velocity of the subject's eye. Further, when the S1 part is associated with an arteriosclerosis index (or an index related to cardiac function), it is possible to evaluate the degree of dynamics of the general circulation from the S1 part extracted based on the time-course changes in the blood flow velocity of the subject's eye.

Figure 14:
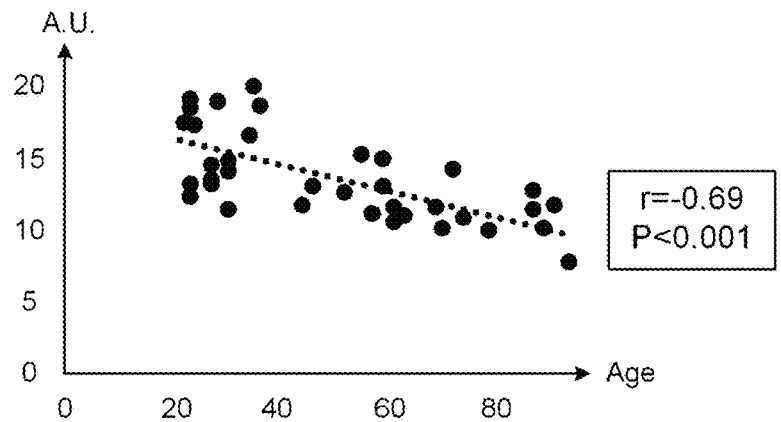
FIG. 14 is a schematic diagram for explaining an operation of the blood flow analysis apparatus according to the embodiments.
Figure 14:
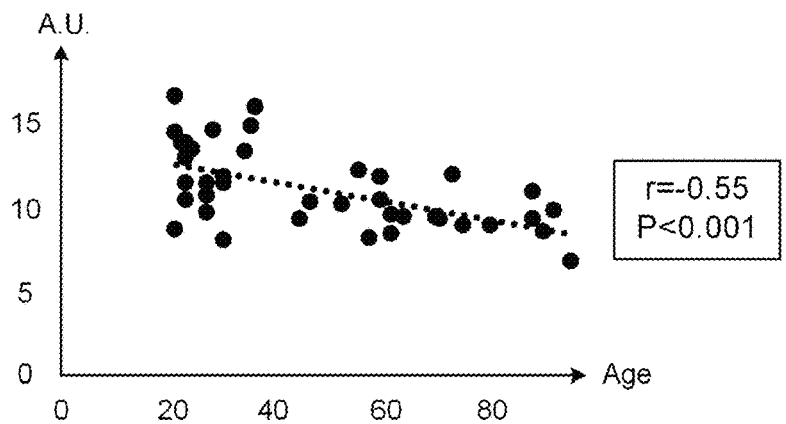
Figure 14:
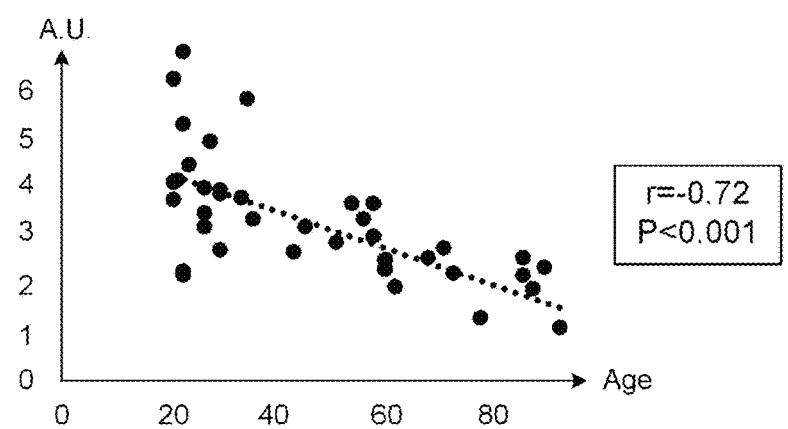

FIG. 14 shows (a) the correlation between the area diastolic Sd and the age, (b) the correlation between the D1 part and the age, and (c) the correlation between the D2 part and the age. In FIG. 14 (a) to (c), the horizontal axis represents the age, while the vertical axis represents arbitrary unit.

From the r values and the P values in (a) to (c) of FIG. 14, the area diastolic Sd has a negative correlation with the age, the D1 part has a negative correlation with the age, and the D2 part has a negative correlation with the age. For example, by specifying the regression line (regression curve) in a plurality of the area diastolics Sd, a plurality of the D1 parts, or a plurality of the D2 parts, it is possible to evaluate whether or not the change in the blood flow velocity of the subject's eye is an age-related change from the area diastolic Sd, the D1 part, or the D2 part extracted based on the time-course changes in the blood flow velocity of the subject's eye. Further, when the area diastolic Sd, the D1 part, or the D2 part is associated with an arteriosclerosis index (or an index related to cardiac function), it is possible to evaluate the degree of dynamics of the general circulation from the area diastolic Sd, the D1 part, or the D2 part extracted based on the time-course changes in the blood flow velocity of the subject's eye.

Figure 15:
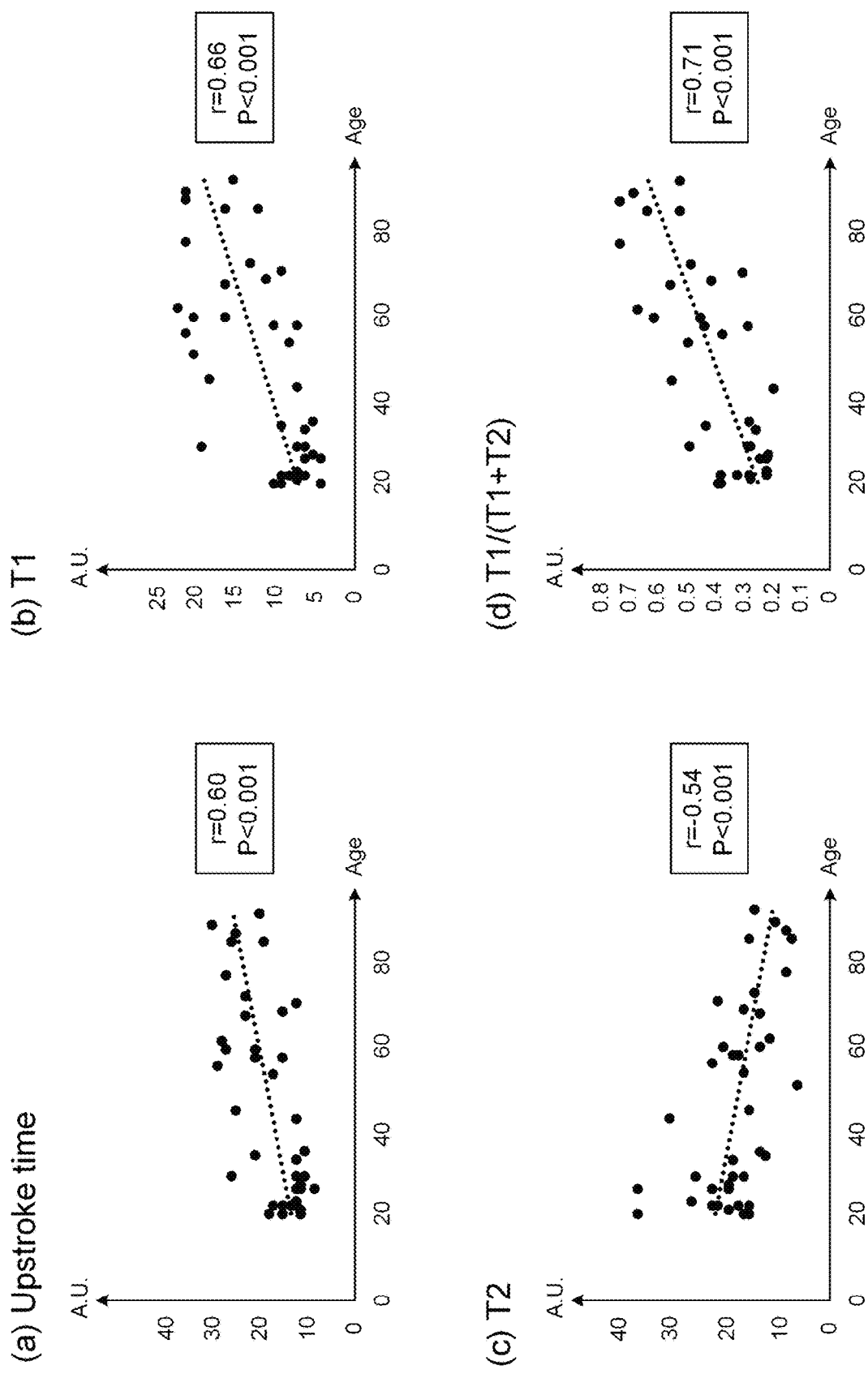
FIG. 15 is a schematic diagram for explaining an operation of the blood flow analysis apparatus according to the embodiments.

FIG. 15 shows (a) the correlation between the upstroke time Tup and the age, (b) the correlation between the half width ascending period T1 and the age, (c) the correlation between the half width descending period T2 and the age, and (d) the correlation between (T1/(T1+T2)) and the age. In FIG. 15 (a) to (d), the horizontal axis represents the age, while the vertical axis represents arbitrary unit.

From the r values and the P values in (a) to (d) of FIG. 15, the upstroke time Tup has a positive correlation with the age, the half width ascending period T1 has a positive correlation with the age, the half width descending period T2 has a negative correlation with the age, and the (T1/(T1+T2)) has a positive correlation with the age. For example, by specifying the regression line (regression curve) in a plurality of the upstroke times Tup, a plurality of the half width ascending periods T1, a plurality of the half width descending periods T2, or a plurality of (T1/(T1+T2)), it is possible to evaluate whether or not the change in the blood flow velocity of the subject's eye is an age-related change from the upstroke time Tup, the half width ascending period T1, the half width descending period T2, or (T1/(T1+T2)) extracted based on the time-course changes in the blood flow velocity of the subject's eye. Further, when the upstroke time Tup, the half width ascending period T1, the half width descending period T2, or (T1/(T1+T2)) is associated with an arteriosclerosis index (or an index related to cardiac function), it is possible to evaluate the degree of dynamics of the general circulation from the upstroke time Tup, the half width ascending period T1, the half width descending period T2, or (T1/(T1+T2)) extracted based on the time-course changes in the blood flow velocity of the subject's eye.

In some embodiments, the parameter evaluation unit 2322 performs an evaluation of the dynamics of the general circulation of the subject based on the results of the evaluation for each of at least two of the above parameters. For example, the parameter evaluation unit 2322 can evaluate whether or not the change in the blood flow velocity of the subject's eye is an age-related change or can evaluate the degree of dynamics of the general circulation, based on a result of the evaluation for a first parameter (e.g., S1 part) and a result of the evaluation for a second parameter (e.g., the half width ascending period T1).

(User Interface 240)

As shown in FIG. 3, The ophthalmologic apparatus 1 is provided with a user interface 240. The user interface 240 includes the display unit 241 and the operation unit 242. The display unit 241 includes a display apparatus 3. The operation unit 242 includes various operation devices and input devices. The user interface 240 may include a device having the output function and the input function integrated together, such as a touch panel display, for example. It is also possible to build embodiments that do not include at least part of the user interface 240. For example, the display device may be an external device connected to the ophthalmologic apparatus.

The ophthalmologic apparatus 1 is an example of the "blood flow analysis apparatus" according to the embodiments. An interface processing unit (not shown) for receiving the blood flow information from outside in the blood flow information analysis processor 232, or the optical system from the objective lens 22 to the OCT unit 100 in FIG. 1 and the arithmetic control unit 200 (image forming unit 220, data processor 230 (blood flow information generation processor 231)) is an example of the "acquisition unit" according to the embodiments. The cardiac cycle specifying unit 2321A is an example of the "specifying unit" according to the embodiments. The parameter evaluation unit 2322 is an example of the "evaluation unit" according to the embodiments. The blood flow information generation processor 231 is an example of the "generator" according to the embodiments.

[Operation]

The operation of the ophthalmologic apparatus 1 according to the embodiments will be described.

Figure 16:
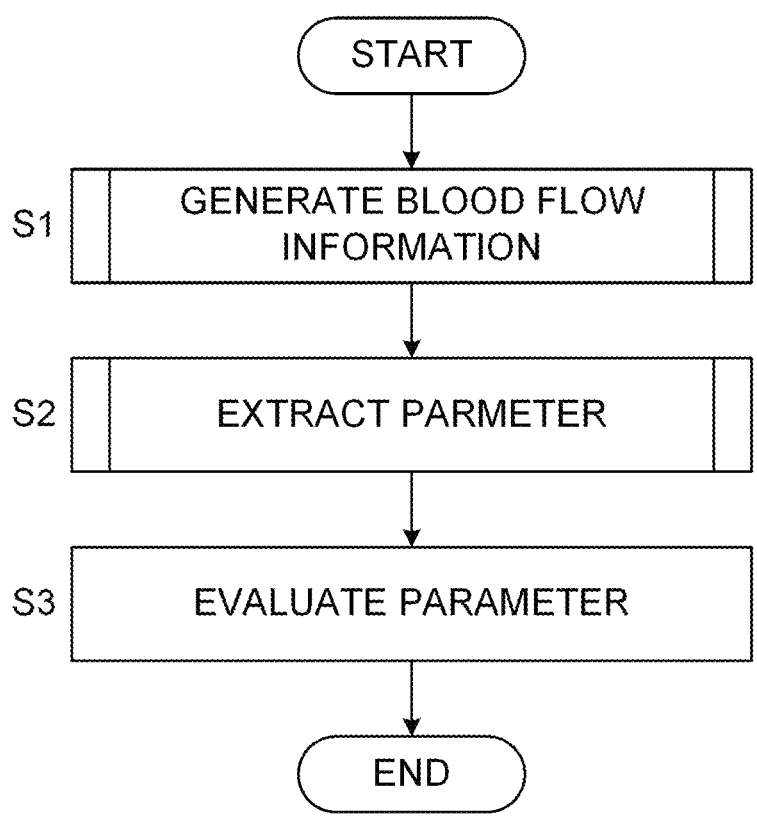
FIG. 16 is a flowchart of an example of the operation of the blood flow analysis apparatus according to the embodiments.
Figure 17:
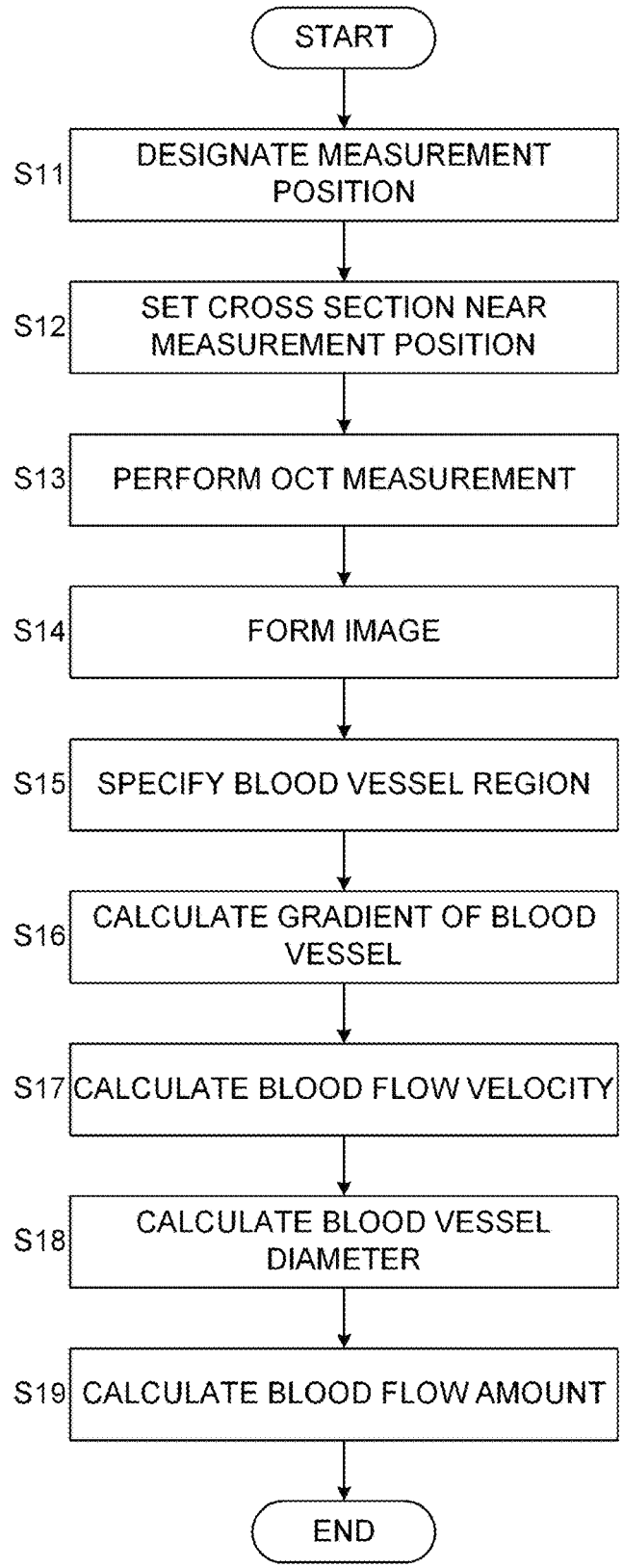
FIG. 17 is a flowchart of an example of the operation of the blood flow analysis apparatus according to the embodiments.
Figure 18:
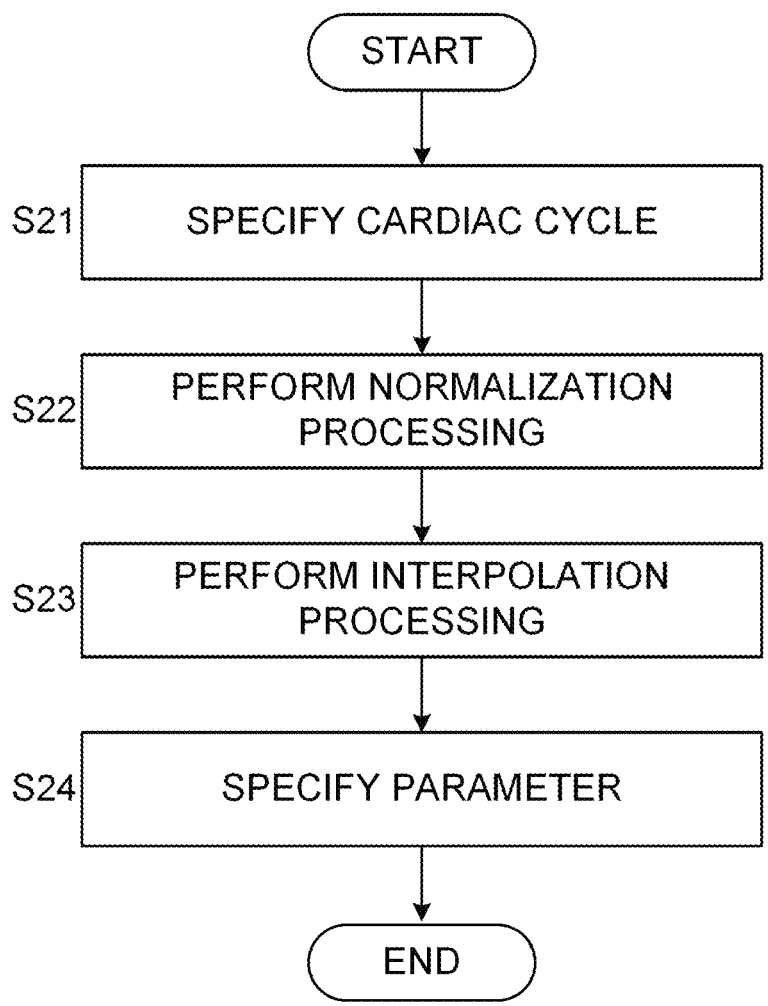
FIG. 18 is a flowchart of an example of the operation of the blood flow analysis apparatus according to the embodiments.

Examples of operations of the ophthalmologic apparatus 1 are illustrated in FIGS. 16 to 18. The storage unit 212 stores computer programs for realizing the processing shown in FIGS. 16 to 18. The main controller 211 operates according to the computer programs, and thereby the main controller 211 performs the processing shown in FIGS. 16 to 18. Noted that it is assumed that general preparatory processes such as alignment, focus adjustment, interference sensitivity adjustment, and z-position adjustment have already been completed.

(S1: Generate Blood Flow Information) First, the controller 210 (main controller 211) controls the blood flow information generation processor 231 to generate the blood flow information representing time-course changes in a blood flow velocity of a single retinal artery or a single retinal vein of the subject's eye.

Specifically, the controller 210 controls the optical system such as the OCT unit 100 to perform OCT measurement, and controls the blood flow information generation processor 231 to generate the blood flow information using the acquired measurement result(s). The details of step S1 will be described later.

(S2: Extract Parameter)

Next, the controller 210 controls the extractor 2321 to extract the one or more parameters described above from the blood flow information acquired in step S1. The details of step S2 will be described later.

(S3: Evaluate Parameter)

Subsequently the controller 210 controls the parameter evaluation unit 2322 to perform predetermined evaluation processing using the parameter(s) obtained in step S2.

As shown in FIGS. 12 to 15, it is assumed that a regression line (regression curve) has been specified in advance for the correlation between the parameter and age corresponding to the predetermined evaluation processing. For example, the parameter evaluation unit 2322 evaluates that the change in the blood flow velocity of the subject's eye is an age-related change when the deviation of the parameter from the regression line is within a predetermined range. Meanwhile, the parameter evaluation unit 2322 evaluates that the change in the blood flow velocity of the subject's eye is not an age-related change when the deviation is outside the predetermined range.

This terminates the operation of the ophthalmologic apparatus 1 (END).

The process of step S1 in FIG. 16 is performed as shown in FIG. 17.

(S11: Designate Measurement Position)

First, the user or the controller 210 sets the scan range for the preliminary measurement. In setting the scan range, for example, the infrared observation image of the fundus Ef acquired in real time or the data of the fundus Ef acquired in the past (fundus image, OCT image, SLO image, phase image, etc.) is referred to.

The controller 210 controls the OCT unit 100 etc. to perform preliminary measurement on the set scan range (a plurality of cross sections). As an example, the set scan range is a three-dimensional region, and the raster scan is repeatedly performed on this three-dimensional region. The phase image forming unit 222 forms the phase image for each of the plurality of cross sections based on the data acquired through the preliminary measurement.

(S12: Set Cross Section Near Measurement Position)

Next, the controller 210 displays the front image of the fundus Ef. The front image is, for example, an infrared observation image acquired in real time, or an image that has been acquired in the past. The user refers to the displayed information and sets the cross section (interested cross section C2) to be the target of the blood flow measurement. For example, by referring to the setting support information displayed together with the front image of the fundus Ef, the user designates a desired artery region (interested blood vessel Db) in the front image.

In the present example, the interested cross section C2 is set manually. However, the embodiments are not limited to this. For example, the interested blood vessel Db and/or the interested cross section C2 can be set automatically based on the infrared observation image and the measurement site information of the fundus Ef. The setting of the interested blood vessel Db is performed, for example, by selecting one of the artery regions (e.g. the thickest one). Further, the interested cross section C2 is, for example, set so as to be orthogonal to the running direction of the interested blood vessel Db at a position where the orientation of the interested blood vessel Db is within tolerance.

Further, the user or the controller 210 (or the data processor 230) sets the cross sections C11 and C12 to be the target of the first scan.

(S13: Perform OCT Measurement)

Subsequently, the controller 210 performs OCT scan (first scan) on the cross sections C11 and C12 set in step S12. Further, the controller 210 performs repetitive OCT scan (second scan) on the interested cross section C2 set in step S12.

(S14: Form Image)

The controller 210 controls the tomographic image forming unit 221 to form the tomographic images G11 and G12 corresponding to the cross sections C11 and C12 based on the data acquired through the first scan in step S13. Further, the controller 210 controls the phase image forming unit 222 to form the phase image of the interested cross section C2 based on the data acquired through the second scan in step S13. In addition, the tomographic image forming unit 221 forms the tomographic image corresponding to the interested cross section C2 based on the same data.

(S15: Specify Blood Vessel Region)

The controller 210 controls the data processor 230 to specify the interested blood vessel Db in the tomographic image formed in step S14. At this time, the controller 210 specifies the image region corresponding to the interested blood vessel Db in the predetermined layer region (e.g., the layer region between the inner border membrane and Bruch membrane) specified by performing segmentation processing by the data processor 230, as the blood vessel region.

(S16: Calculate Gradient of Blood Vessel)

Subsequently, the controller 210 controls the gradient calculator 2312 to calculate the gradient "U" of the interested blood vessel Db at the interested cross section C2, as described above.

(S17: Calculate Blood Flow Velocity)

Subsequently, the controller 210 controls the blood flow velocity calculator 2313 to calculate the blood flow velocity at the interested cross section C2, based on the gradient "U" calculated based on the first scan in step S13 and the phase image acquired through the second scan in step S13.

(S18: Calculate Blood Vessel Diameter)

Next, the controller 210 controls the blood vessel diameter calculator 2314 to calculate the diameter of the interested blood vessel Db at the interested cross section C2.

(S19: Calculate Blood Flow Amount)

Subsequently, the controller 210 controls the blood flow amount calculator 2315 to calculate the flow amount of the blood flowing in the interested blood vessel Db, based on the blood flow velocity calculated in step S17 and the blood vessel diameter calculated in step S18.

The controller 210 controls the blood flow information generation processor 231 to generate the blood flow information including the time-series blood flow velocity over a period longer than at least one cardiac cycle.

This terminates the processing of step S1 in FIG. 16 (END).

The process of step S2 in FIG. 16 is performed as shown in FIG. 18.

(S21: Specify Cardiac Cycle)

First, the controller 210 controls the blood flow information generation processor 231 to specify the blood flow information representing the time-course changes in the blood flow velocity from the blood flow information obtained in step S1 of FIG. 16, and controls the cardiac cycle specifying unit 2321A to specify the cardiac cycle from the specified blood flow information as described above.

(S22: Perform Normalization Processing)

Next, the controller 210 controls the normalization unit 2321B to normalize the time-course changes in the blood flow velocity within the cardiac cycle specified in step S21, as described above.

(S23: Perform Interpolation Processing)

Subsequently, the controller 210 controls the interpolation unit 2321C to interpolate the time-course changes in the blood flow velocity normalized in step S21, as described above.

(S24: Specify Parameter)

The controller 210 controls the extractor 2321 to specify the parameter(s) shown in FIGS. 11A and 11B from the time-course changes in the blood flow velocity interpolated in step S23. The extractor 2321 outputs the specified parameter(s) to the parameter evaluation unit 2322.

The parameter evaluation unit 2322 performs evaluation processing described above using the parameter(s) extracted in step S24, in step S3.

This terminates the processing of step S2 in FIG. 16 (END).

[Actions]

Actions of the blood flow analysis apparatus, the blood flow analysis method, and the program according to the embodiments will be described.

A blood flow analysis apparatus (ophthalmologic apparatus 1) includes an acquisition unit (interface processing unit for receiving the blood flow information from outside in the blood flow information analysis processor 232, or the optical system from the objective lens 22 to the OCT unit 100 and the arithmetic control unit 200 (image forming unit 220, data processor 230 (blood flow information generation processor 231)) and an extractor (2321). The acquisition unit is configured to acquire blood flow information (blood flow velocity variation information) representing time-course changes in a blood flow velocity of a single retinal artery or a single retinal vein. The extractor is configured to extract one or more parameters corresponding to change in the blood flow velocity from the blood flow information.

According to such a configuration, the one or more parameters corresponding to the change in the blood flow velocity are extracted from the time-course changes in blood flow velocity of the single retinal artery or the single retinal vein. Thereby, the parameter(s) for evaluating the dynamics of the general circulation caused by a blood flow in the retinal artery or the retinal vein in the fundus with high accuracy can be extracted.

In the blood flow analysis apparatus according to some embodiments, the extractor includes a specifying unit (cardiac cycle specifying unit 2321A) configured to specify a cardiac cycle based on the blood flow information, and is configured to extract the one or more parameters based on the time-course changes in the blood flow velocity within the cardiac cycle.

According to such a configuration, the one or more parameters corresponding to the change in the blood flow velocity within the cardiac cycle is extracted. Thereby, the parameter(s) for evaluating the dynamics of the general circulation caused by the beating of the heart, the state of the blood vessel, or the like with high accuracy can be extracted.

In the blood flow analysis apparatus according to some embodiments, the extractor includes a normalization unit (2321B) configured to normalize an amplitude of the blood flow velocity and the cardiac cycle based on the blood flow information, and is configured to extract the one or more parameters based on the time-course changes in the blood flow velocity normalized by the normalization unit.

According to such a configuration, the parameter(s) useful for a plurality of subjects with different blood flow velocities and cardiac cycles can be extracted. Thereby, the dynamics of the general circulation can be evaluated with high accuracy, using the time-course changes in the blood flow velocities of a plurality of subjects (eyes of the subjects).

In the blood flow analysis apparatus according to some embodiments, the extractor includes an interpolation unit (2321C) configured to interpolate the blood flow velocity so that a sampling number of the blood flow velocity within the cardiac cycle becomes a predetermined measurement sampling number, and is configured to extract the one or more parameters based on the time-course changes in the blood flow velocity interpolated by the interpolation unit.

According to such a configuration, the parameter(s) can be extracted from the blood flow information having a fixed number of the measurement samplings for a plurality of subjects with different blood flow velocities and cardiac cycles. Thereby, the dynamics of the general circulation can be evaluated with high accuracy, using the time-course changes in the blood flow velocities of a plurality of subjects (eyes of the subjects).

In the blood flow analysis apparatus according to some embodiments, the one or more parameters include an upstroke time (Tup) from a start timing of the cardiac cycle to a peak arrival timing of the blood flow velocity, a first time (T1) from a timing when the blood flow velocity becomes a first blood flow velocity ($V_{50}$) during a rising period of the blood flow velocity to the peak arrival timing (Tp), and a second time (T2) from the peak arrival timing to a timing when the blood flow velocity becomes the first blood flow velocity during a falling period of the blood flow velocity after the peak arrival timing.

According to such a configuration, the blood flow analysis apparatus for evaluating the dynamics of the general circulation of the subject with high accuracy using the above upstroke time, the first time, or the second time can be provided.

In the blood flow analysis apparatus according to some embodiments, the one or more parameters include an area under waveform of the time-course changes in the blood flow velocity during diastolic phase (Sd), an area under waveform of the time-course changes in blood flow velocity during the first half of the diastolic phase (D1 part), and an area under waveform of the time-course changes in the blood flow velocity during the second half of the diastolic phase (D2 part).

According to such a configuration, the blood flow analysis apparatus for evaluating the dynamics of the general circulation of the subject with high accuracy using the area under waveform of the time-course changes in the blood flow velocity during diastolic phase, the area under waveform of the time-course changes in blood flow velocity during the first half of the diastolic phase, or the area under waveform of the time-course changes in the blood flow velocity during the second half of the diastolic phase can be provided.

The blood flow analysis apparatus according to some embodiments includes an evaluation unit (parameter evaluation unit 2322) configured to evaluate whether or not the change in the blood flow velocity is an age-related change that changes with aging based on the one or more parameters.

According to such a configuration blood flow analysis apparatus for evaluating whether or not the change in the blood flow velocity is an age-related change with high accuracy can be provided.

In the blood flow analysis apparatus according to some embodiments, the retinal artery or the retinal vein is an artery or a vein in a layer region between inner limiting membrane and Bruch membrane.

According to such a configuration, the parameter(s) for evaluating the dynamics of the general circulation caused by the blood flow in the artery or the vein in the layer region between inner limiting membrane and Bruch membrane with high accuracy can be extracted.

The blood flow analysis apparatus according to some embodiments includes a generator (blood flow information generation processor 231) configured to generate the blood flow information based on a plurality of signals obtained by performing optical coherence tomography on approximately the same measurement site at different timings.

According to such a configuration, the blood flow information representing the time-course changes in the blood flow velocity of the single retinal artery or the single retinal vein is generated, and the one or more parameters corresponding to the change in the blood flow velocity are extracted from the generated blood flow information. Thereby, the blood flow analysis apparatus capable of extracting the parameter(s) for evaluating the dynamics of the general circulation caused by the blood flow in the retinal artery or the retinal vein in the fundus with high accuracy can be provided.

A blood flow analysis method according to some embodiments includes an acquisition step of acquiring blood flow information representing time-course changes in a blood flow velocity of a single retinal artery or a single retinal vein and an extraction step of extracting one or more parameters corresponding to change in the blood flow velocity from the blood flow information.

According to such a method, the one or more parameters corresponding to the change in the blood flow velocity are extracted from the time-course changes in blood flow velocity of the single retinal artery or the single retinal vein. Thereby, the parameter(s) for evaluating the dynamics of the general circulation caused by a blood flow in the retinal artery or the retinal vein in the fundus with high accuracy can be extracted.

In the blood flow analysis method according to some embodiments, the extraction step includes a specifying step of specifying a cardiac cycle based on the blood flow information, and is performed to extract the one or more parameters based on the time-course changes in the blood flow velocity within the cardiac cycle.

According to such a method, the one or more parameters corresponding to the change in the blood flow velocity within the cardiac cycle is extracted. Thereby, the parameter(s) for evaluating the dynamics of the general circulation caused by the beating of the heart, the state of the blood vessel, or the like with high accuracy can be extracted.

In the blood flow analysis method according to some embodiments, the extraction step includes a normalization step of normalizing an amplitude of the blood flow velocity and the cardiac cycle based on the blood flow information, and is performed to extract the one or more parameters based on the time-course changes in the blood flow velocity normalized in the normalization step.

According to such a method, the parameter(s) useful for a plurality of subjects with different blood flow velocities and cardiac cycles can be extracted. Thereby, the dynamics of the general circulation can be evaluated with high accuracy, using the time-course changes in the blood flow velocities of a plurality of subjects (eyes of the subjects).

In the blood flow analysis method according to some embodiments, the extraction step includes an interpolation step of interpolating the blood flow velocity so that a sampling number of the blood flow velocity within the cardiac cycle becomes a predetermined measurement sampling number, and is performed to extract the one or more parameters based on the time-course changes in the blood flow velocity interpolated in the interpolation step.

According to such a method, the parameter(s) can be extracted from the blood flow information having a fixed number of the measurement samplings for a plurality of subjects with different blood flow velocities and cardiac cycles. Thereby, the dynamics of the general circulation can be evaluated with high accuracy, using the time-course changes in the blood flow velocities of a plurality of subjects (eyes of the subjects).

In the blood flow analysis method according to some embodiments, the one or more parameters include an upstroke time (Tup) from a start timing of the cardiac cycle to a peak arrival timing of the blood flow velocity, a first time (T1) from a timing when the blood flow velocity becomes a first blood flow velocity ($V_{50}$) during a rising period of the blood flow velocity to the peak arrival timing (Tp), and a second time (T2) from the peak arrival timing to a timing when the blood flow velocity becomes the first blood flow velocity during a falling period of the blood flow velocity after the peak arrival timing.

According to such a method, the blood flow analysis method for evaluating the dynamics of the general circulation of the subject with high accuracy using the above upstroke time, the first time, or the second time can be provided.

In the blood flow analysis method according to some embodiments, the one or more parameters include an area under waveform of the time-course changes in the blood flow velocity during diastolic phase (Sd), an area under waveform of the time-course changes in blood flow velocity during the first half of the diastolic phase (D1 part), and an area under waveform of the time-course changes in the blood flow velocity during the second half of the diastolic phase (D2 part).

According to such a method, the blood flow analysis method for evaluating the dynamics of the general circulation of the subject with high accuracy using the area under waveform of the time-course changes in the blood flow velocity during diastolic phase, the area under waveform of the time-course changes in blood flow velocity during the first half of the diastolic phase, or the area under waveform of the time-course changes in the blood flow velocity during the second half of the diastolic phase can be provided.

The blood flow analysis method according to some embodiments includes an evaluation step of evaluating whether or not the change in the blood flow velocity is an age-related change that changes with aging based on the one or more parameters.

According to such a method, the blood flow analysis method for evaluating whether or not the change in the blood flow velocity is an age-related change with high accuracy can be provided.

In the blood flow analysis method according to some embodiments, the retinal artery or the retinal vein is an artery or a vein in a layer region between inner limiting membrane and Bruch membrane.

According to such a method, the parameter(s) for evaluating the dynamics of the general circulation caused by the blood flow in the artery or the vein in the layer region between inner limiting membrane and Bruch membrane with high accuracy can be extracted.

The blood flow analysis method according to some embodiments includes a generation step of generating the blood flow information based on a plurality of signals obtained by performing optical coherence tomography on approximately the same measurement site at different timings.

According to such a method, the blood flow information representing the time-course changes in the blood flow velocity of the single retinal artery or the single retinal vein is generated, and the one or more parameters corresponding to the change in the blood flow velocity are extracted from the generated blood flow information. Thereby, the blood flow analysis method capable of extracting the parameter(s) for evaluating the dynamics of the general circulation caused by the blood flow in the retinal artery or the retinal vein in the fundus with high accuracy can be provided.

A program according to some embodiments causes a computer to execute each step of any one of the blood flow analysis method described in any one of the above.

According to such a program, the one or more parameters corresponding to the change in the blood flow velocity are extracted from the time-course changes in blood flow velocity of the single retinal artery or the single retinal vein. Thereby, the parameter(s) for evaluating the dynamics of the general circulation caused by a blood flow in the retinal artery or the retinal vein in the fundus with high accuracy can be extracted.

It is possible to create a computer-readable, non-transitory recording medium that records the program for any of the embodiments. This non-transitory storage medium may be in any form, examples of which include magnetic disks, optical disks, magneto-optical disks, and semiconductor memory.

The embodiments described above are merely examples. One who intends to implement the present invention may arbitrarily modify (omission, replacement, addition, etc.) within the scope of the invention.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A blood flow analysis apparatus, comprising:
   processing circuitry configured to acquire blood flow information representing time-course changes in a blood flow velocity of a single retinal artery or a single retinal vein; and
   the processing circuitry is further configured to extract one or more parameters corresponding to change in the blood flow velocity from the blood flow information, wherein
   the processing circuitry is further configured to specify a cardiac cycle based on the blood flow information, and to extract the one or more parameters based on the time-course changes in the blood flow velocity within the cardiac cycle, and
   the one or more parameters include an upstroke time from a start timing of the cardiac cycle to a peak arrival timing of the blood flow velocity, a first time from a timing when the blood flow velocity becomes a first blood flow velocity during a rising period of the blood flow velocity to the peak arrival timing, and a second time from the peak arrival timing to a timing when the blood flow velocity becomes the first blood flow velocity during a falling period of the blood flow velocity after the peak arrival timing.

2. The blood flow analysis apparatus of claim 1, wherein the processing circuitry is further configured to normalize an amplitude of the blood flow velocity and the cardiac cycle based on the blood flow information, and to extract the one or more parameters based on the time-course changes in the normalized blood flow velocity.

3. The blood flow analysis apparatus of claim 1, wherein the processing circuitry is further configured to interpolate the blood flow velocity so that a sampling number of the blood flow velocity within the cardiac cycle becomes a predetermined measurement sampling number, and to extract the one or more parameters based on the time-course changes in the interpolated blood flow velocity.

4. The blood flow analysis apparatus of claim 1, wherein the one or more parameters include an area under waveform of the time-course changes in the blood flow velocity during diastolic phase, an area under waveform of the time-course changes in blood flow velocity during the first half of the diastolic phase, and an area under waveform of the time-course changes in the blood flow velocity during the second half of the diastolic phase.

5. The blood flow analysis apparatus of claim 1, wherein the processing circuitry is further configured to evaluate whether or not the change in the blood flow velocity is an age-related change that changes with aging based on the one or more parameters.

6. The blood flow analysis apparatus of claim 1, wherein the retinal artery or the retinal vein is an artery or a vein in a layer region between inner limiting membrane and Bruch membrane.

7. The blood flow analysis apparatus of claim 1, further comprising
   a generator configured to generate the blood flow information based on a plurality of signals obtained by performing optical coherence tomography on approximately the same measurement site at different timings.

8. A blood flow analysis method, comprising:
   an acquisition step of acquiring blood flow information representing time-course changes in a blood flow velocity of a single retinal artery or a single retinal vein; and
   an extraction step of extracting one or more parameters corresponding to change in the blood flow velocity from the blood flow information, wherein
   the extraction step includes a specifying step of specifying a cardiac cycle based on the blood flow information, and is performed to extract the one or more parameters based on the time-course changes in the blood flow velocity within the cardiac cycle, and
   the one or more parameters include an upstroke time from a start timing of the cardiac cycle to a peak arrival timing of the blood flow velocity, a first time from a timing when the blood flow velocity becomes a first blood flow velocity during a rising period of the blood flow velocity to the peak arrival timing, and a second time from the peak arrival timing to a timing when the blood flow velocity becomes the first blood flow velocity during a falling period of the blood flow velocity after the peak arrival timing.

9. The blood flow analysis method of claim 8, wherein the extraction step includes a normalization step of normalizing an amplitude of the blood flow velocity and the cardiac cycle based on the blood flow information, and is performed to extract the one or more parameters based on the time-course changes in the blood flow velocity normalized in the normalization step.

10. The blood flow analysis method of claim 8, wherein the extraction step includes an interpolation step of interpolating the blood flow velocity so that a sampling number of the blood flow velocity within the cardiac cycle becomes a predetermined measurement sampling number, and is performed to extract the one or more parameters based on the time-course changes in the blood flow velocity interpolated in the interpolation step.

11. The blood flow analysis method of claim 8, wherein the one or more parameters include an area under waveform of the time-course changes in the blood flow velocity during diastolic phase, an area under waveform of the time-course changes in blood flow velocity during the first half of the diastolic phase, and an area under waveform of the time-course changes in the blood flow velocity during the second half of the diastolic phase.

12. The blood flow analysis method of claim 8, further comprising
an evaluation step of evaluating whether or not the change in the blood flow velocity is an age-related change that changes with aging based on the one or more parameters.

13. The blood flow analysis method of claim 8, wherein the retinal artery or the retinal vein is an artery or a vein in a layer region between inner limiting membrane and Bruch membrane.

14. The blood flow analysis method of claim 8, further comprising
a generation step of generating the blood flow information based on a plurality of signals obtained by performing optical coherence tomography on approximately the same measurement site at different timings.

15. A computer readable non-transitory recording medium in which a program for causing
a computer to execute each step of the blood flow analysis method of claim 8 is recorded.

* * * * *